(12) United States Patent
Zhang

(10) Patent No.: US 12,331,136 B2
(45) Date of Patent: Jun. 17, 2025

(54) ANTI-AGING STURGEON ROE TETRAPEPTIDE AND PREPARATION METHOD AND APPLICATION THEREOF

(71) Applicant: Shenzhen Porshealth Bioengineering Co., Ltd., Shenzhen (CN)

(72) Inventor: Silu Zhang, Shenzhen (CN)

(73) Assignee: Shenzhen Porshealth Bioengineering Co., Ltd., Shenzhen (CN)

( * ) Notice: Subject to any disclaimer, the term of this patent is extended or adjusted under 35 U.S.C. 154(b) by 0 days.

(21) Appl. No.: 18/650,574

(22) Filed: Apr. 30, 2024

(65) Prior Publication Data
US 2024/0317802 A1    Sep. 26, 2024

(30) Foreign Application Priority Data
Dec. 12, 2023    (CN) .......................... 202311694439.4

(51) Int. Cl.
| | | |
|---|---|---|
| *C07K 5/103* | (2006.01) | |
| *A61K 8/64* | (2006.01) | |
| *A61K 38/00* | (2006.01) | |
| *A61P 39/06* | (2006.01) | |
| *A61Q 19/08* | (2006.01) | |
| *C12P 21/06* | (2006.01) | |

(52) U.S. Cl.
CPC .............. *C07K 5/1005* (2013.01); *A61K 8/64* (2013.01); *A61P 39/06* (2018.01); *A61Q 19/08* (2013.01); *C12P 21/06* (2013.01); *A61K 38/00* (2013.01); *A61K 2800/782* (2013.01)

(58) Field of Classification Search
CPC ......... C07K 5/1005; A61P 39/06; A61K 8/64; A61K 38/00; A61K 2800/782; A61Q 19/08; C12P 21/06
See application file for complete search history.

(56) References Cited

U.S. PATENT DOCUMENTS

| | | |
|---|---|---|
| 2014/0242013 A1 | 8/2014 | Yu et al. |
| 2022/0087926 A1 | 3/2022 | Zou et al. |
| 2022/0347250 A1 | 11/2022 | Chen et al. |

OTHER PUBLICATIONS

Noman et al, Influence of Degree of Hydrolysis on Chemical Composition, Functional Properties, and Antioxidant Activities of Chinese Sturgeon (Acipenser sinensis) Hydrolysates Obtained by Using Alcalase 2.4L, Journal of Aquatic Food Product Technology, 2019, 28, pp. 583-597.*
CNIPA, Notification of First Office Action for Chinese application CN202311694439.4, Jan. 16, 2024.
CNIPA, Notification to grant patent right for Chinese application CN202311694439.4, Feb. 6, 2024.

* cited by examiner

*Primary Examiner* — Li N Komatsu
(74) *Attorney, Agent, or Firm* — Hemisphere Law, PLLC; Zhigang Ma

(57) ABSTRACT

The present invention discloses an anti-aging sturgeon roe tetrapeptide, having a peptide sequence of NLPL (SEQ ID NO: 9). The present invention further discloses a preparation method of the anti-aging sturgeon roe tetrapeptide, specifically comprising the following steps: (1) adding deionized water to sturgeon roes and homogenizing to obtain a sturgeon roe homogenate; (2) adjusting a pH value of the sturgeon roe homogenate, adding alkaline protease, performing enzymolysis and enzyme inactivation, and cooling to obtain sturgeon roe enzymatic hydrolysate; and (3) centrifuging the sturgeon roe enzymatic hydrolysate, taking a supernatant to obtain anti-aging sturgeon roe tetrapeptide, and storing for later use. The sturgeon roe peptide prepared by the present invention can improve the levels of oxidative stress and skin related factors (type I collagen and hyaluronic acid) by adjusting a cell proliferation state, so as to realize the protective effect on skin cells at a cellular level.

8 Claims, 25 Drawing Sheets
Specification includes a Sequence Listing.

ANTI-AGING STURGEON ROE TETRAPEPTIDE AND PREPARATION METHOD AND APPLICATION THEREOF

REFERENCE TO SEQUENCE LISTING

The substitute sequence listing is submitted as a XML file filed via EFS-Web, with a file name of "Substitute Sequence_Listing.XML", a creation date of Mar. 1, 2025, and a size of 15857 bytes. The substitute sequence Listing filed via EFS-Web is a part of the specification and is incorporated in its entirety by reference herein.

TECHNICAL FIELD

The present invention relates to the technical field of bioactive peptides, in particular to an anti-aging sturgeon roe tetrapeptide and a preparation method and application thereof.

BACKGROUND

Skin aging is the external manifestation of human aging. A mechanism of aging is complex. Research in recent years has shown that the pathogenesis may be related to many factors, including lipid metabolism, oxidative stress, inflammation, apoptosis, etc. Research has shown that the main reason for skin aging is that the oxygen free radicals produced by ultraviolet rays and other factors affect the normal growth cycle of skin cells, promote the hydrolysis of collagen and other extracellular matrix by protease, and cause DNA damage and the reduction of matrix protein synthesis, thereby resulting in skin relaxation and reduction of elasticity. With the stimulation of facial muscle fibers by expressions, the most significant sign of skin aging, i.e., wrinkles are produced.

Mechanism of endogenous skin aging: endogenous aging of skin is an irreversible and slow physiological process. Endogenous skin aging is evident only after a certain stage of age, and is characterized by skin drying, roughness, elasticity reduction, and the production of wrinkles. With the increase of age, the dermal mast cells and fibroblasts in the skin tissue are decreased, the secretion of collagen is decreased, and the dermo-epidermal junction area is flattened. Under the influence of aging of other organs in a human body, endogenous skin aging is caused by many factors. From the perspective of the physiological mechanism, oxidative stress causes damage to DNA, protein and other components of cells, and exacerbates progressive telomere shortening, which is an important reason for endogenous skin aging.

Exogenous skin aging: exogenous factors, such as ultraviolet irradiation, pollution and smoking, produce a series of reactions such as pro-oxidation/anti-oxidation through neuroendocrine immune regulation, and affect cell renewal, so as to permanently affect the physiological function of the skin. Ultraviolet induced photoaging is the currently recognized most important cause of skin aging.

Reactive oxygen species (ROS) produced by UV induction can damage DNA and inhibit tyrosine phosphatases, which leads to signal transduction enhancement and ultimately leads to up-regulation of the transcription factor AP-1. At the same time, ultraviolet ray can also lead to the up-regulation of c-Jun as one of the components of AP-1, and down-regulation of retinoic acid receptors, to further weaken the inhibitory effect of retinoic acid on AP-1. Moreover, ultraviolet ray directly induces DNA variation, up-regulates nuclear factor-kB (NF-KB), and inhibits transforming growth factor-β (TGF-β)—mediated cell signaling pathways. These effects lead to degradation or secretion decrease of collagen. Collagen as the most widespread matrix protein of the body provides the support and elasticity for skin. Once the balance of collagen secretion/degradation is broken, the content of collagen in the skin will be reduced, thereby affecting the stability of the skin structure. With the excessive stimulation of the fiber by muscle movement such as expression muscle, the most significant sign of skin aging, i.e., wrinkles are produced. Therefore, the synergistic use of active ingredients with multiple action mechanisms is a preferred choice to achieve a desired anti-aging effect.

Functional extracts separated from aquatic food can be used as functional food and nutritional health products. Peptides obtained from aquatic protein by biotechnology means not only show high nutritional value, but also show biological characteristics for diet or therapeutic purposes, have special active aquatic extracts, and may become functional food for human nutrition. Fish is the earliest biological resource that people begin to eat and rich in protein, vitamins and minerals, and is a high-quality raw material for the development of functional foods such as oligopeptide. At present, a large number of antioxidant, antitumor, antibacterial and anti-inflammatory polypeptides have been obtained by enzymolysis and separation from silver carp, Pacific saury, tilapia and the like, and new structures and mechanisms of action have been continuously discovered. Therefore, rational and efficient development and utilization of freshwater fish resources has broad market prospects, and has certain social and economic significance.

However, there is no relevant report on the research of anti-aging effect of sturgeon roe polypeptide.

Therefore, how to prepare a sturgeon roe polypeptide with anti-aging effect is an urgent problem for those skilled in the art.

SUMMARY

In view of this, a purpose of the present invention is to provide an anti-aging sturgeon roe tetrapeptide and a preparation method and application thereof, so as to solve the deficiencies in the prior art.

In order to achieve the above purpose, the present invention adopts the following technical solution:

An anti-aging sturgeon roe tetrapeptide has a peptide sequence of NLPL (SEQ ID NO: 9).

A preparation method of the anti-aging sturgeon roe tetrapeptide specifically comprises the following steps:
(1) adding deionized water to sturgeon roes and homogenizing to obtain a sturgeon roe homogenate;
(2) adjusting a pH value of the sturgeon roe homogenate, adding alkaline protease (ALEALASE™), performing enzymolysis and enzyme inactivation, and cooling to obtain sturgeon roe enzymatic hydrolysate;
(3) centrifuging the sturgeon roe enzymatic hydrolysate, taking a supernatant to obtain anti-aging sturgeon roe tetrapeptide, and storing for later use.

Further, in the above step (1), a mass ratio of the sturgeon roes to the deionized water is 1:6.

Further, in the above step (1), rotational speed of homogenizing is 8000 rpm and time is 1 min.

Further, in the above step (2), an addition amount of the alkaline protease is 1%.

Further, in the above step (2), temperature of enzymolysis is 55° C. and time is 8 h.

Further, in the above step (2), temperature of enzyme inactivation is 90-100° C. and time is 10-15 min.

Further, in the above step (2), cooling is performed to room temperature.

Further, in the above step (3), temperature of centrifugal treatment is 4° C., rotational speed is 8000 rpm, and time is 15 min.

Further, in the above step (3), temperature of storage is −80° C.

The present invention further requests to protect an application of the above sturgeon roe tetrapeptide or the sturgeon roe tetrapeptide prepared by the above preparation method in preparation of anti-aging drugs, anti-aging food, anti-aging health products or anti-aging cosmetics.

According to the above technical solution, compared with the prior art, the present invention has the following beneficial effects:

The present invention evaluates the protein content, hydrolysis degree, protein recovery rate, ABTS antioxidant activity and tyrosinase inhibitory activity of sturgeon roe peptide, selects the enzyme addition amount of 1% (according to substrate mass), enzymolysis time of 8 h and solid-liquid ratio of 1:6, and selects the alkaline protease as the preparation condition of a sturgeon roe peptidyl delivery system. The obtained enzymolysis product of the sturgeon roes has high lipid content.

The sturgeon roe peptide prepared by the present invention can improve the levels of oxidative stress and skin related factors (type I collagen and hyaluronic acid) by adjusting a cell proliferation state, so as to realize the protective effect on skin cells at a cellular level.

According to the results of animal experiments, the sturgeon roes prepared by the present invention can realize the anti-aging effect by adjusting the oxidative stress and the skin state in small aging water bodies.

Based on a virtual selection means, the present invention finds that the anti-aging tetrapeptide NLPL (SEQ ID NO: 9) derived from sturgeon can play an important anti-aging role in the body, has high absorption efficiency, and can play an important role in the body.

DESCRIPTION OF DRAWINGS

FIG. 16C also shows the effect of sturgeon enzymatic hydrolysate on lactate dehydrogenase (LDH) in damaged cells;

DETAILED DESCRIPTION

Figure 1:
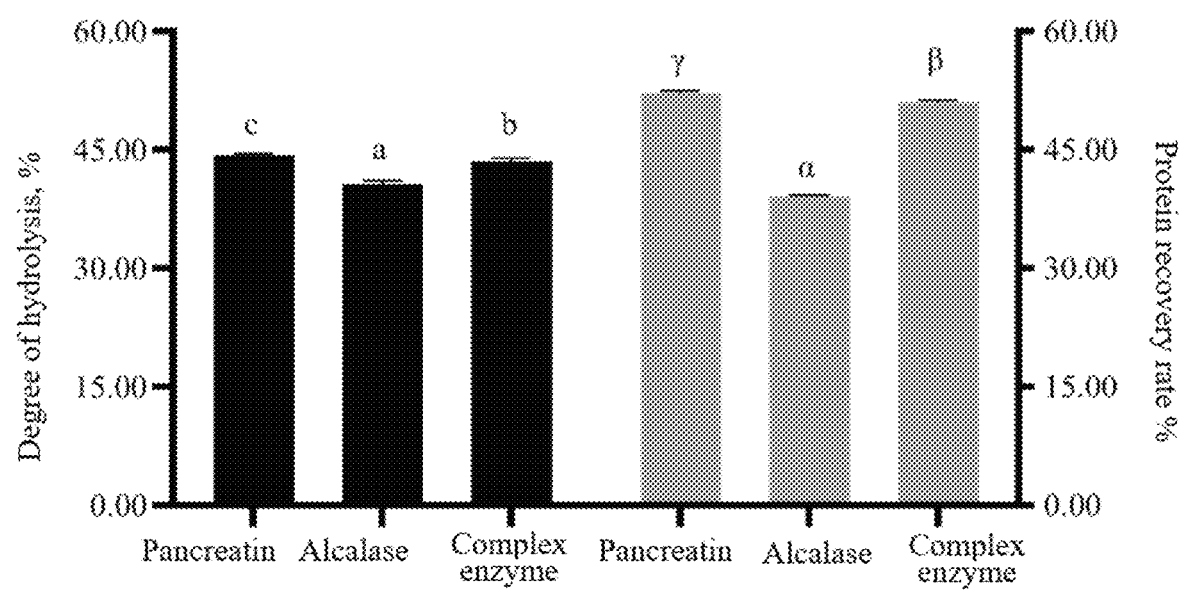
FIG. 1 shows the degree of hydrolysis and protein recovery of enzyme types.

Technical solutions in the embodiments of the present invention are described clearly and fully below. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiment 1

A preparation method of anti-aging sturgeon roe tetrapeptide specifically comprises the following steps:
(1) adding 6 times the mass of deionized water to sturgeon roes and homogenizing at 8000 rpm for 1 min to obtain a sturgeon roe homogenate;
(2) adjusting the sturgeon roe homogenate to an optimal pH value, adding 1% alkaline protease, placing in a thermostatic oscillator for enzymolysis at 55° C. for 8 h, then placing in a boiling water bath for enzyme inactivation at 90° C. for 15 min, and cooling to room temperature to obtain sturgeon roe enzymatic hydrolysate;
(3) centrifuging the sturgeon roe enzymatic hydrolysate at 4° C. and 8000 rpm for 15 min, taking a supernatant to obtain anti-aging sturgeon roe tetrapeptide and storing −80° C. for later use.

Embodiment 2

A preparation method of anti-aging sturgeon roe tetrapeptide specifically comprises the following steps:
(1) adding 6 times the mass of deionized water to sturgeon roes and homogenizing at 8000 rpm for 1 min to obtain a sturgeon roe homogenate;
(2) adjusting the sturgeon roe homogenate to an optimal pH value, adding 1% alkaline protease, placing in a thermostatic oscillator for enzymolysis at 55° C. for 8 h, then placing in a boiling water bath for enzyme inactivation at 95° C. for 12 min, and cooling to room temperature to obtain sturgeon roe enzymatic hydrolysate;
(3) centrifuging the sturgeon roe enzymatic hydrolysate at 4° C. and 8000 rpm for 15 min, taking a supernatant to obtain anti-aging sturgeon roe tetrapeptide and storing −80° C. for later use.

Embodiment 3

A preparation method of anti-aging sturgeon roe tetrapeptide specifically comprises the following steps:
(1) adding 6 times the mass of deionized water to sturgeon roes and homogenizing at 8000 rpm for 1 min to obtain a sturgeon roe homogenate;
(2) adjusting the sturgeon roe homogenate to an optimal pH value, adding 1% alkaline protease, placing in a thermostatic oscillator for enzymolysis at 55° C. for 8 h, then placing in a boiling water bath for enzyme inactivation at 100° C. for 10 min, and cooling to room temperature to obtain sturgeon roe enzymatic hydrolysate;
(3) centrifuging the sturgeon roe enzymatic hydrolysate at 4° C. and 8000 rpm for 15 min, taking a supernatant to obtain anti-aging sturgeon roe tetrapeptide and storing −80° C. for later use.

Performance Test
I. Process Optimization
1.1 Enzymolysis Process

The research aims to optimize the hydrolysis conditions of sturgeon roes to obtain bioactive peptide. The experimental design covers the changes of different enzyme types, enzymolysis time, enzyme addition amount and solid-liquid ratio.

Firstly, 10 g of sturgeon roes are taken, added with ultra-pure water and homogenized for 1 min at 8000 rpm. Then, the optimal pH value is adjusted, enzymes are added, and a sample is hydrolyzed in a thermostatic oscillator at 55° C. Subsequently, the sample is placed in the boiling water bath for enzyme inactivation at 90-100° C. for 10-15 min. After cooling to room temperature, centrifugal treatment is carried out at 4° C. and 8000 rpm for 15 min. The supernatant is taken for the subsequent determination of indexes, and then stored at −80° C. for use.

1.2 Single Factor Investigation

Single factor investigation of enzyme type: in the single factor research of enzyme type, the addition amount of enzyme is 1%, the hydrolysis time is 4 h, and the solid-liquid ratio is 1:6. The effects of different proteases (trypsin, alkaline protease and complex enzyme with trypsin-alkaline protease 1:1) on hydrolysis are tested.

Single factor investigation of enzymolysis time: another single factor research aims to determine the effect of the enzymolysis time on peptide production. Under the condition that the solid-liquid ratio is 1:6 and the addition amount of enzyme is 1%, alkaline protease is used for hydrolysis, and the hydrolysis time is set as 2 h, 4 h, 8 h, 12 h and 16 h, respectively.

Single factor investigation of addition amount of enzyme: the influence of the addition amount of enzyme on hydrolysis effect is evaluated through single factor research. The solid-liquid ratio is kept at 1:6; alkaline protease is used for hydrolysis for 8 h; and 0.2%, 0.5%, 0.8%, 1% and 2% of addition amount of enzyme are added respectively.

Single factor investigation of solid-liquid ratio: finally, the influence of the solid-liquid ratio on hydrolysis effect is investigated by single factor analysis. The sturgeon roe samples are mixed with 20 mL, 40 mL and 60 mL of water respectively, and then hydrolyzed with 1% alkaline protease for 8 h.

1.3 Determination of Degree of Hydrolysis and Protein Recovery Rate

The degree of hydrolysis is determined by OPA method, and the protein content of fish roe and enzymolysis supernatant is determined by Kjeldahl method in GB 5009.5-2016 *National Food Safety Standard-Determination of Protein in Foods*.

$$\text{Protein recovery rate \%} = \text{protein content of enzymolysis supernatant/protein content of fish roe} \times 100\%.$$

1.4 Antioxidant Capacity of Fish Roe Enzymolysis Supernatant ABTS

A method for determining ABTS free radical scavenging capacity is an experimental method for evaluating the antioxidant capacity of a compound or sample. ABTS (2,2'-azino-bis(3-ethylbenzothiazoline) is a synthetic free radical compound that can be used to simulate oxygen free radicals in living organisms. In the method, the antioxidant performance of the compound is judged by measuring the scavenging ability of the compound for ABTS free radicals. In the determination process, ABTS free radicals will change the color, and the addition of antioxidants will cause color fading, the degree of which is in direct proportion to the antioxidant capacity. The basic steps of the method include:
① Preparing ABTS solution: making ABTS react with hydrogen peroxide to produce a blue free radical solution, and then diluting with a certain proportion of solvent to obtain a suitable concentration.
② Mixing a sample to be tested: mixing a compound to be tested with the diluted ABTS solution.
③ Measuring absorbance: within a period of time, measuring the absorbance change of the mixture to determine the scavenging ability of ABTS free radicals, that is, the antioxidant capacity.

In this experiment, the ABTS free radical scavenging ability of the enzymolysis supernatant is determined with reference to the optimized method.

1.5 Tyrosinase Inhibitory Activity
1.5.1 Solution Preparation

L-tyrosine solution: weighing 0.025 g of L-tyrosine into 50 mL of sterile ionized water, dissolving with a phosphate buffer solution, and fixing a volume to 50 mL, for use right after it is ready.

Tyrosinase solution: preparing the tyrosinase with the phosphate buffer solution at 1000 U/mL and storing away from light at −20° C., for use right after it is ready.

Sample solution: diluting the sample with PBS buffer salt solution to a concentration of 1 mg/mL, for use right after it is ready.

1.5.2 Test Steps

By referring to the addition amounts of reagents in Table 1, the L-tyrosine solution, the sample solution/reagent and the phosphate buffer solution are added into the reaction system successively, thoroughly mixed, incubated in a constant temperature environment at 37° C. for 10 min, then added with 20 μL of tyrosinase solution into each well successively, and uniformly mixed at 37° C. to react for 5 min. A microplate reader is immediately put and the absorbance is tested at 475 nm.

TABLE 1

Sample Addition of Tyrosinase Activity Inhibition Reaction System

| Reagent | Solvent base well ($T_a$) | Solvent reaction well ($T_b$) | Sample base well ($T_c$) | Sample reaction well ($T_d$) |
|---|---|---|---|---|
| L-tyrosine solution (μL) | 0 | 40 | 0 | 40 |
| Sample solution (μL) | 0 | 0 | 40 | 40 |
| Solvent (phosphate buffer solution) (μL) | 40 | 40 | 0 | 0 |
| Phosphate buffer solution (μL) | 70 | 30 | 70 | 30 |

1.6 Experimental Results and Discussion 1.6.1 Single Factor Investigation Results of Sturgeon 1.6.1.1 Single Factor Investigation Results of Sturgeon-Enzyme Types The degree of hydrolysis and protein recovery rate of enzyme types are shown in FIG. 1.

It can be seen from FIG. 1 that through analysis from the perspective of the degree of hydrolysis and the protein recovery rate, the degree of hydrolysis and the protein recovery rate of sturgeon roes enzymatically hydrolyzed by pancreatic enzyme are the highest, while the degree of hydrolysis and the protein recovery rate of sturgeon roes enzymatically hydrolyzed by alkaline protease are the lowest, but the difference in the protein recovery rate between the two is not obvious. This will provide consideration for the screening of enzyme types.

Figure 2:
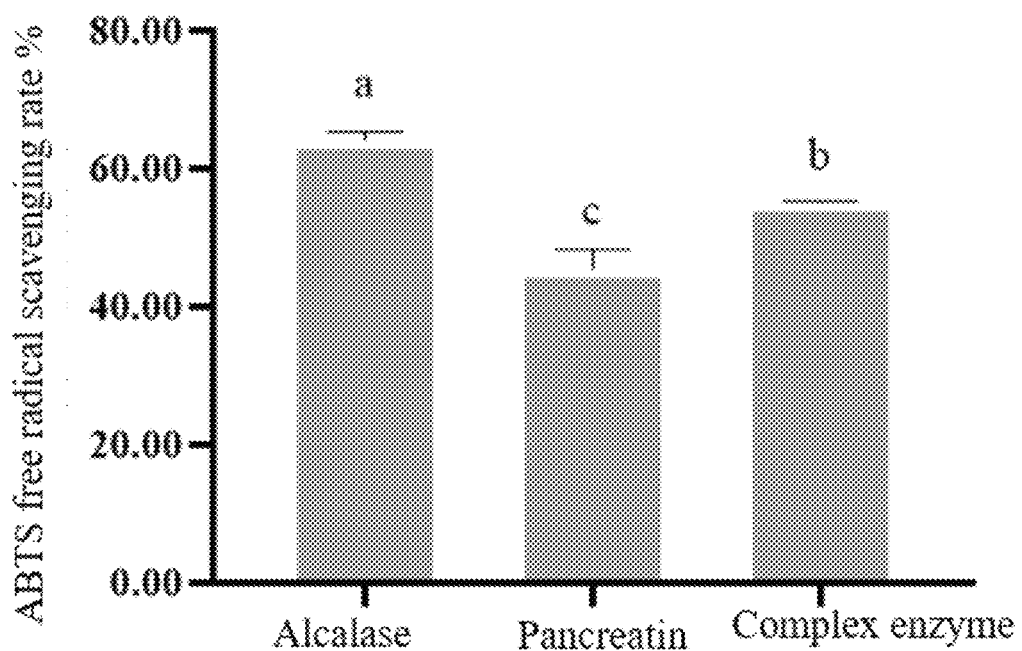
FIG. 2 shows the ABTS free radical scavenging activity of enzyme types.

The ABTS free radical scavenging activity of the enzyme types are shown in FIG. 2.

It can be seen from FIG. 2 that the ABTS antioxidant activity of sturgeon roe peptides enzymatically hydrolyzed by alkaline protease is the highest and had obvious advantages.

Figure 3:
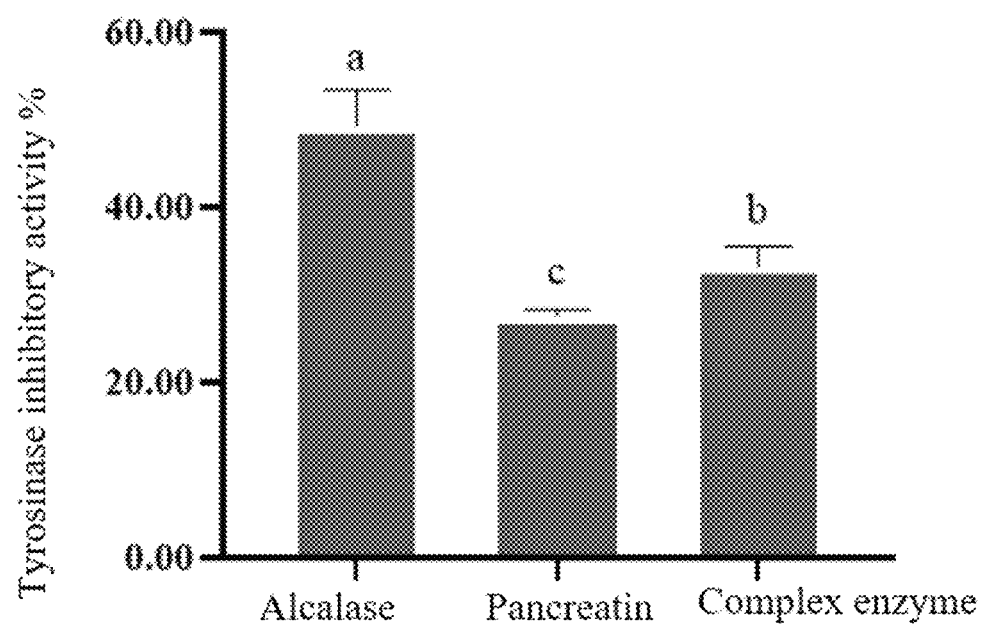
FIG. 3 shows the tyrosinase inhibitory activity of enzyme types.

The tyrosinase inhibitory activity of the enzyme types is shown in FIG. 3.

It can be seen from FIG. 3 that the sturgeon roe peptide enzymatically hydrolyzed by alkaline protease has the highest tyrosinase inhibitory activity. Combined with the analysis of ABTS antioxidant activity, the sturgeon roe peptide enzymatically hydrolyzed by alkaline protease also has the highest ABTS antioxidant activity, and the tyrosinase inhibitory activity has a trend of being positively correlated with the ABTS antioxidant activity. Considering the degree of hydrolysis and the protein recovery rate, alkaline protease is selected as the condition for next step of process optimization.

1.6.1.2 Single Factor Investigation Results of Sturgeon-Enzymolysis Time

Figure 4:
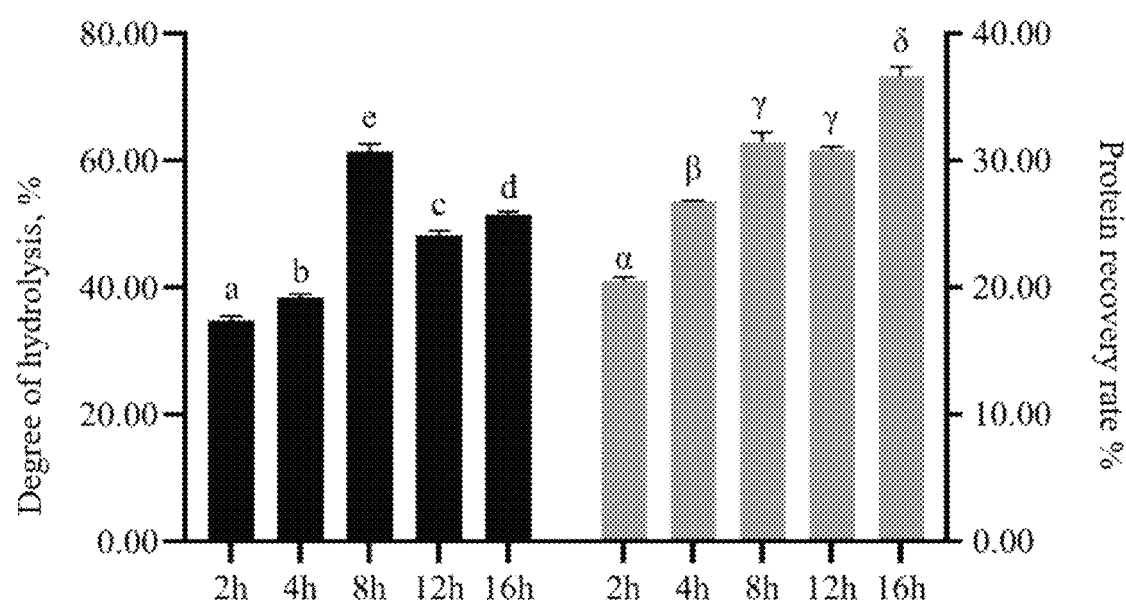
FIG. 4 shows the degree of hydrolysis and protein recovery at enzymolysis time.

The protein recovery rate and the degree of hydrolysis at enzymolysis time are shown in FIG. 4.

It can be seen from FIG. 4 that it is found from comprehensive analysis of the degree of hydrolysis and the protein recovery rate at different enzymolysis time that the protein recovery rate at 8 h is the highest, and the degree of hydrolysis is the highest at 16 h.

Figure 5:
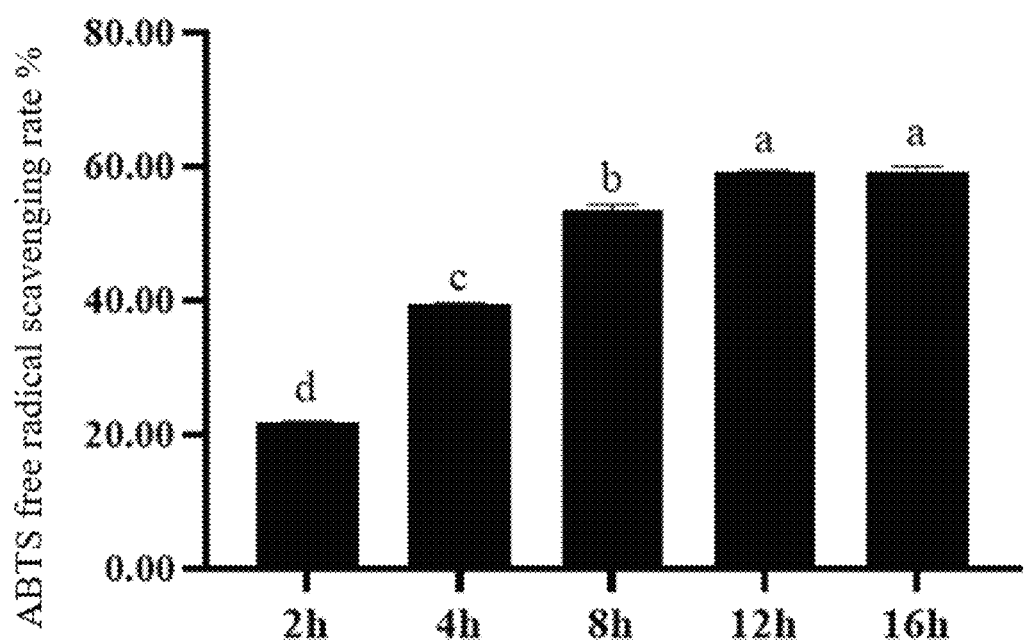
FIG. 5 shows ABTS free radical scavenging activity at enzymolysis time.

The ABTS free radical scavenging activity at enzymolysis time is shown in FIG. 5.

It can be seen from FIG. 5 that from the results of ABTS antioxidant activity at different enzymolysis time, the scavenging rate of ABTS is increased with the increase of the enzymolysis time. However, there is no significant change in ABTS scavenging rate after 8 h. Through analysis from the perspective of cost of process production, the selection of enzymolysis time of 8 h is more suitable for lower production cost.

Figure 6:
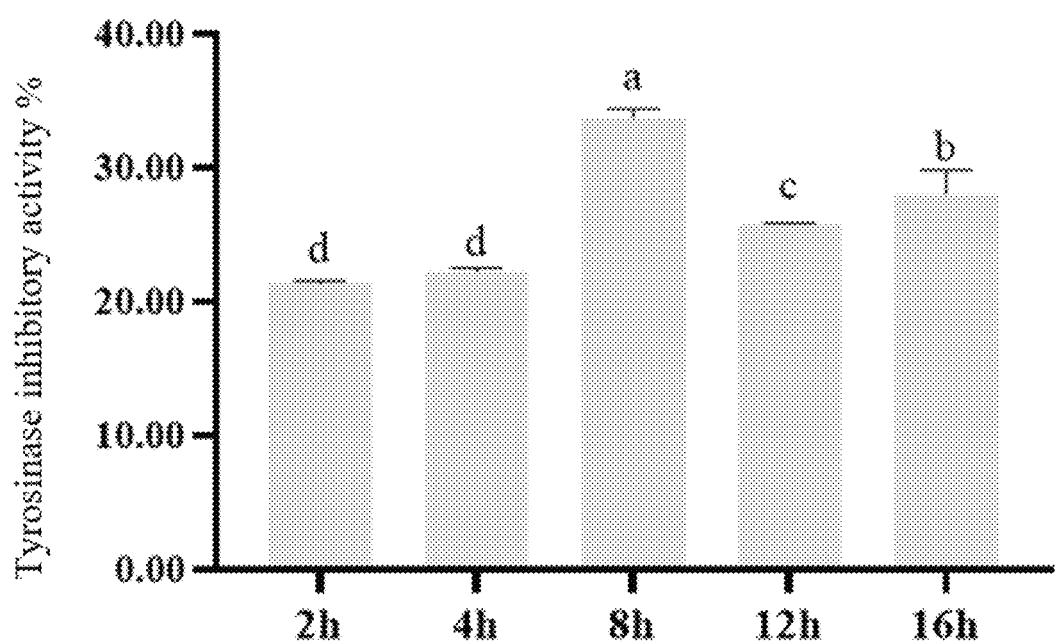
FIG. 6 shows tyrosinase inhibitory activity at enzymolysis time.

Tyrosinase inhibitory activity at enzymolysis time is shown in FIG. 6.

It can be seen from FIG. 6 that through analysis from the results of different time, the tyrosinase inhibitory activity is the highest when the enzymolysis time is 8 h. Combined with the results of the ABTS antioxidant activity, the selection of enzymolysis time of 8 h can make the sturgeon roe peptide have higher ABTS antioxidant activity and tyrosinase inhibitory activity. Moreover, 8 h enzymolysis also makes sturgeon roes have the highest degree of hydrolysis and better protein recovery rate, and the production cost is more reasonable.

Figure 7:
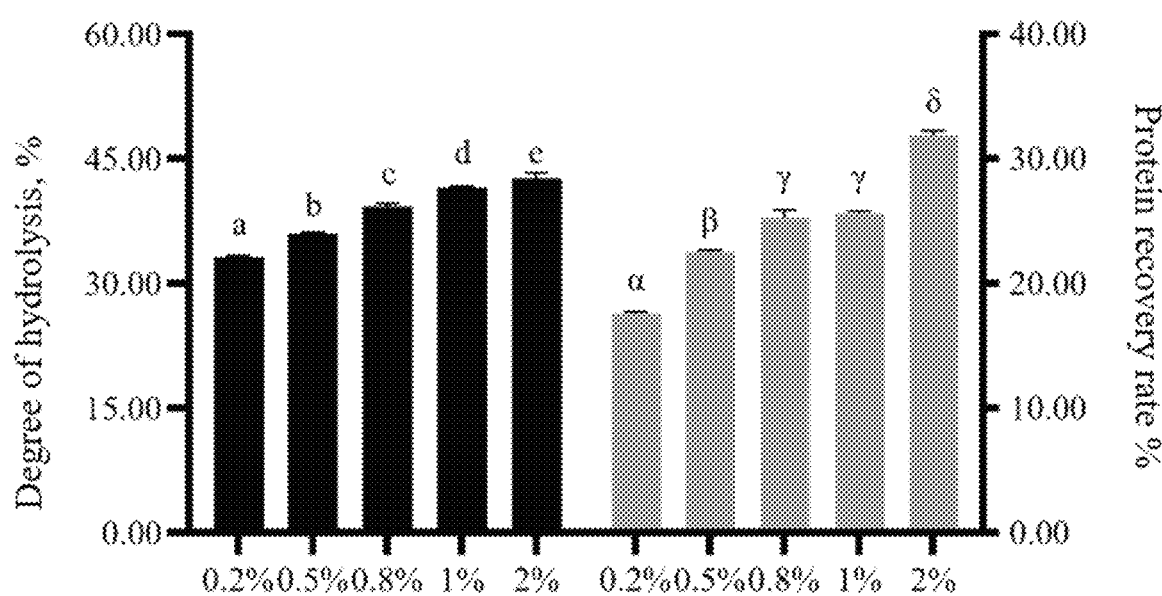
FIG. 7 shows the degree of hydrolysis and protein recovery with the addition amount of enzyme.

1.6.1.3 Single Factor Investigation Results of Sturgeon-Addition Amount of Enzyme The degree of hydrolysis and the protein recovery rate of the addition amount of enzyme are shown in FIG. 7.

It can be seen from FIG. 7 that through analysis from the perspective of the degree of hydrolysis and the protein recovery rate, the degree of hydrolysis and the protein recovery rate of the sturgeon roe peptide both show an increasing trend with the increase of the addition amount of enzyme.

Figure 8:
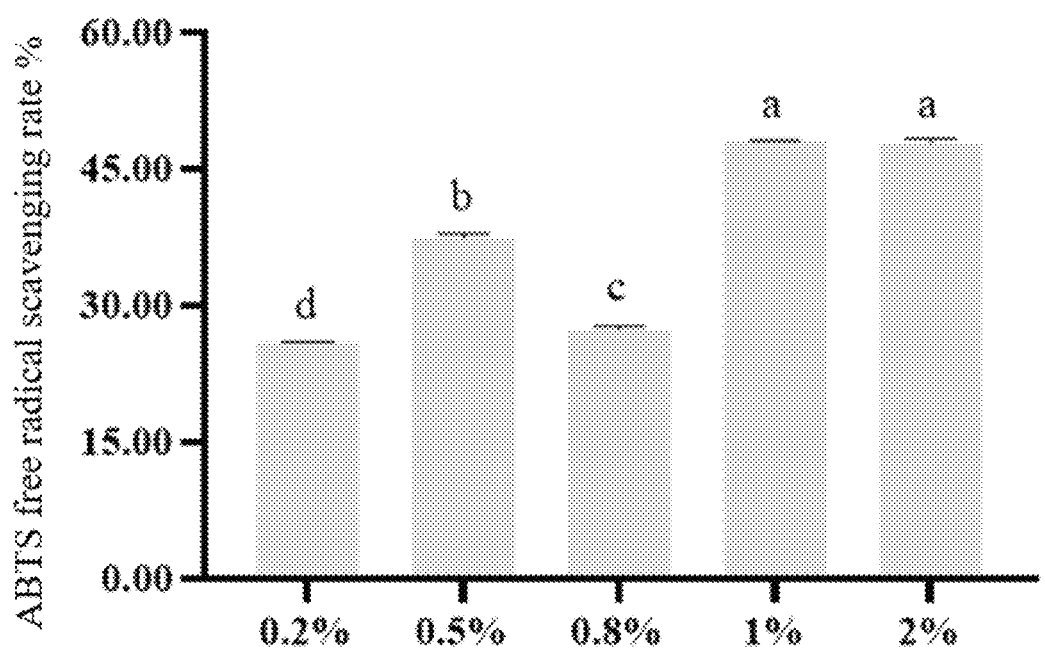
FIG. 8 shows ABTS free radical scavenging activity with the addition amount of enzyme.

The ABTS free radical scavenging activity of the addition amount of enzyme is shown in FIG. 8.

It can be seen from FIG. 8 that the ABTS antioxidant activity of the sturgeon roe peptide with the addition amount 1% of enzyme is the highest, and there is no significant difference from the activity of the sturgeon roe peptide with the addition amount 2% of enzyme.

Figure 9:
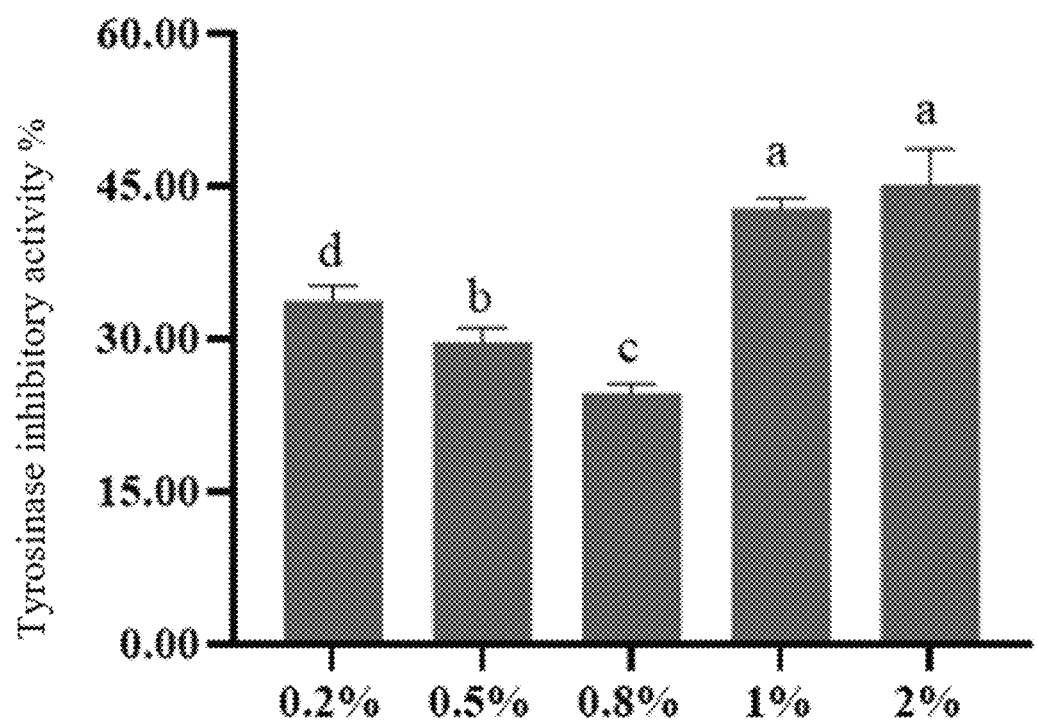
FIG. 9 shows tyrosinase inhibitory activity with the addition amount of enzyme.

The tyrosinase inhibitory activity with the addition amount of enzyme is shown in FIG. 9.

It can be seen from FIG. 9 that the tyrosinase inhibitory activity of the sturgeon roe peptide with the addition amount 2% of enzyme is higher than that of 1% roe peptide, but there is no significant difference. However, the ABTS antioxidant activity of the fish roe peptide with the addition amount 1% of enzyme is not different from that of the fish roe peptide with the addition amount 2% of enzyme, and the fish roe peptide with the addition amount 1% of enzyme has better degree of hydrolysis and protein recovery rate. To sum up, from the perspective of the cost of process production, it is more advantageous to select addition amount 1% of enzyme for next step of optimization.

1.6.1.4 Single Factor Investigation Results of Sturgeon-Solid-Liquid Ratio

Figure 10:
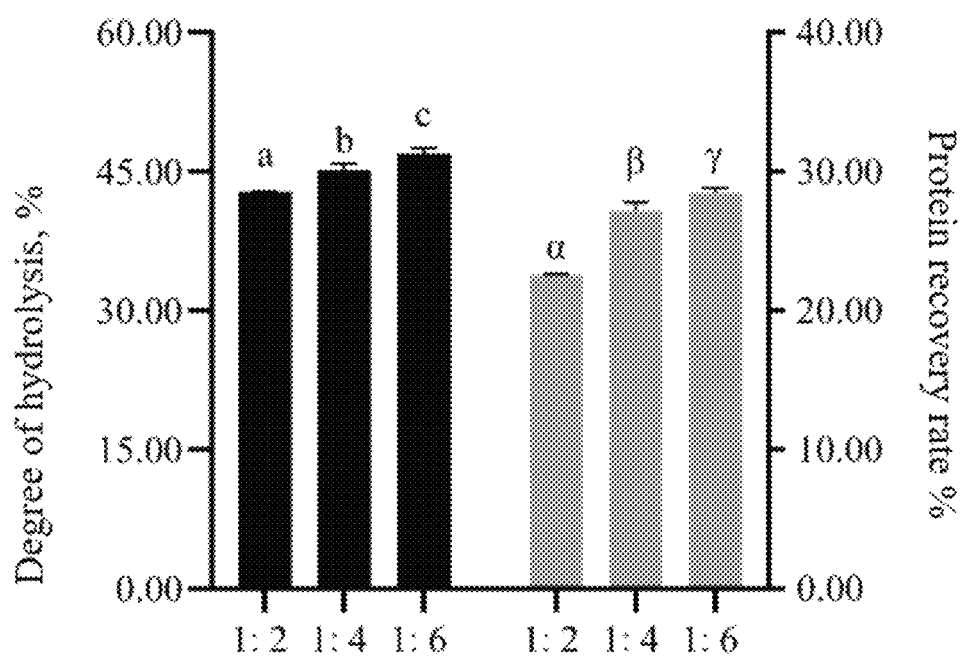
FIG. 10 shows the degree of hydrolysis and protein recovery at a solid-liquid ratio.

The degree of hydrolysis and the protein recovery rate of the solid-liquid ratio are shown in FIG. 10.

It can be seen from FIG. 10 that the protein recovery rate is 1:2<1:4<1:6, which may be due to the decrease of the solid-liquid ratio, which affects the reaction between sturgeon roes and protease, resulting in the decrease of the protein recovery rate of the enzymolysis solution. The increase of the solid-liquid ratio can increase the reaction surface area between sturgeon roes and protease, so that the enzymolysis is more sufficient and more small molecule active peptides are released, thereby enhancing the activity of the enzymolysis solution; and the degree of hydrolysis is also increased with the increase of the solid-liquid ratio.

Figure 11:
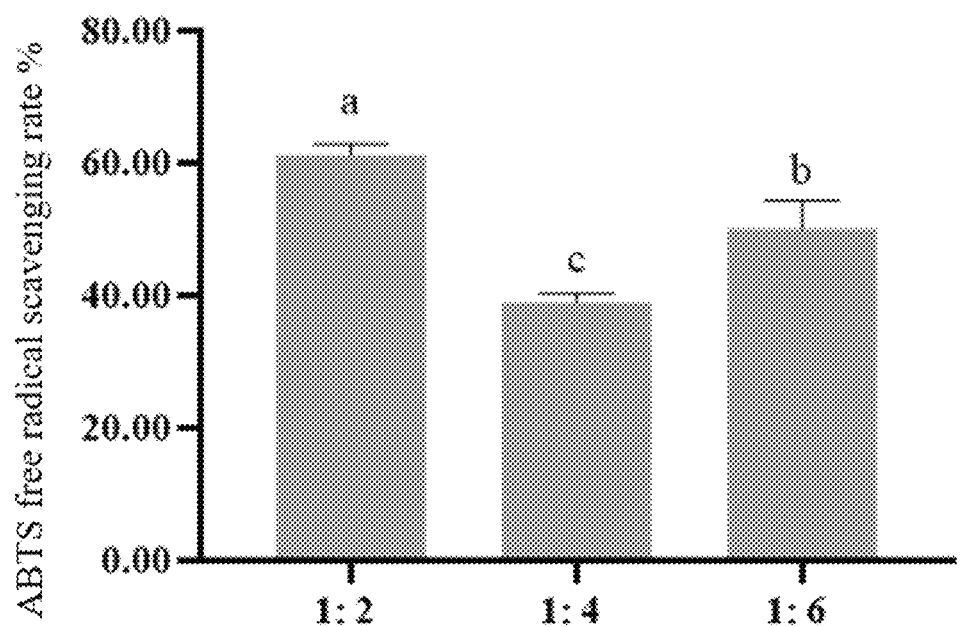
FIG. 11 shows ABTS free radical scavenging activity at a solid-liquid ratio.

The ABTS free radical scavenging activity of the solid-liquid ratio is shown in FIG. 11.

It can be seen from FIG. 11 that the ABTS scavenging rate is 1:2>1:6>1:4, which should be screened in combination with the protein recovery rate and the tyrosinase inhibitory activity.

Figure 12:
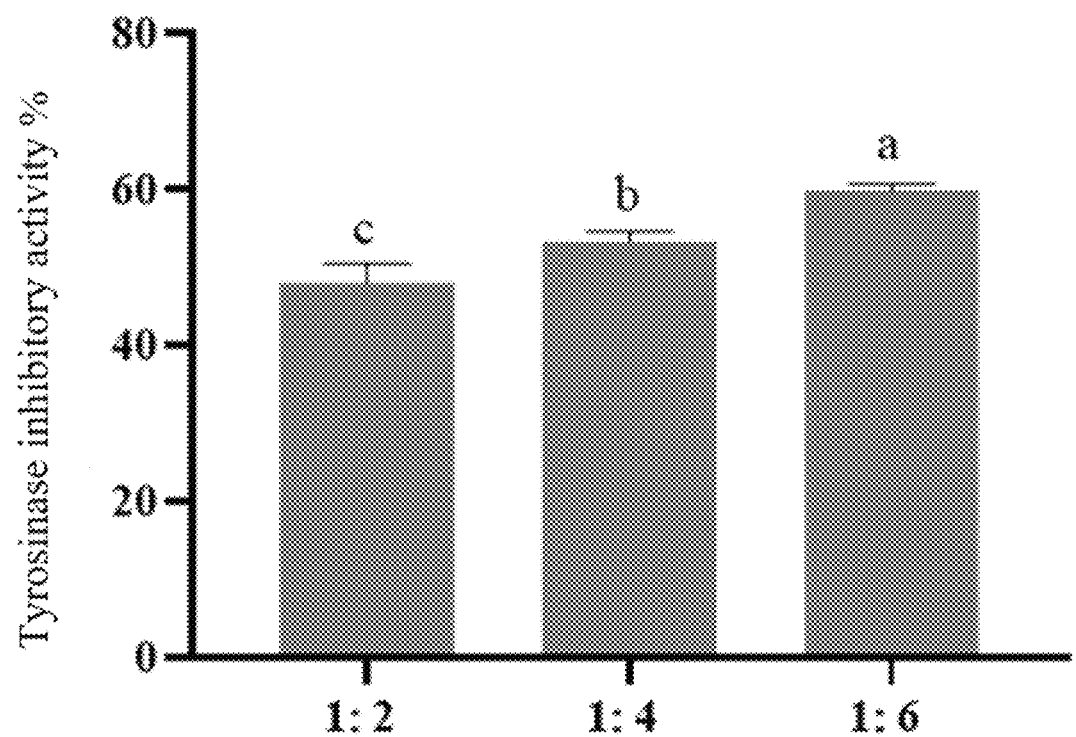
FIG. 12 shows tyrosinase inhibitory activity at a solid-liquid ratio.

The tyrosinase inhibitory activity of the solid-liquid ratio is shown in FIG. 12.

It can be seen from FIG. 12 that the tyrosinase inhibitory activity of the enzymolysis solution with different solid-liquid ratio is: 1:6>1:4>1:2, which is in direct proportion to the protein recovery rate. It is speculated that with the increase of the solid-liquid ratio, the surface area of the contact reaction between sturgeon roes and protease is larger, which makes the reaction more sufficient and thorough, thereby releasing more sturgeon roe peptide with tyrosinase inhibitory activity and enhancing the tyrosinase inhibitory activity. Combined with the antioxidant activity and protein recovery rate of ABTS, the solid-liquid ratio of 1:6 is selected for the next step of process optimization.

1.7 Analysis of Unsaturated Fatty Acid 1.7.1 Fat Extraction

A 250 mL flat-bottomed flask is made at constant weight and weighed. The sample is weighed into a 50 mL colorimetric tube, added with 2 mL of 95% ethanol and 4 mL of water, and mixed uniformly. 10 mL of hydrochloric acid solution is added and mixed uniformly. The colorimetric tube is placed in a water bath at 70-80° C. and hydrolyzed for 40 min. The flask is oscillated every 10 min to mix the particles attached to the flask wall into the solution. After hydrolysis, the colorimetric tube is taken out and cooled to room temperature.

10 mL of 95% ethanol is added and mixed uniformly. 30 mL of ether and petroleum ether mixture is added, covered, shaken for 5 min and stood for 10 min. The ether layer extract is collected into a 250 mL flask. The hydrolysate is extracted repeatedly for 3 times according to the above steps, and the ether layer is steamed in a water bath. The residue is the fat extract. The flask is dried in an oven at 60° C. to constant weight and weighed.

The fat contents of sturgeon roes and freeze-dried enzymolysis solution are shown in Table 2.

TABLE 2

Fat Contents of Sturgeon Roes and Freeze-Dried Enzymolysis Solution

| | Fat Contents/% |
|---|---|
| Sturgeon roes | 13.68 ± 0.94 |
| Freeze-dried enzymolysis solution of sturgeon roes | 30.02 ± 1.87 |

1.7.2 Fatty Acid Methylation 4 mL of 0.5 mol/L sodium methanol is added to the flask and heated in a water bath at 45° C. for 20 min. The sample liquid in the flask is transferred into a 20 mL colorimetric tube and 4 mL of 14% boron trifluoride methanol solution is added and heated in a water bath at 45° C. for 20 min. The colorimetric tube is cooled to room temperature, added with 3 mL of n-hexane to extract for 2 min, and stood for stratification; then, n-hexane layer is taken for measurement.

1.7.3 Computer Analysis

The initial temperature of the injection volume is 100° C. for 13 min; the temperature is raised to 180° C. at 10° C./min for 6 min, raised to 192° C. at 1° C./min for 9 min, and raised to 240° C. at 4° C./min for 2 min. Chromatographic column operation conditions are as follows: sample volume is 1 μL; a shunt ratio is 20:1; the injection temperature is 260° C.; ion source temperature is 240° C.; SCAN full scan mode; and a scan range is 40 to 400. The result is expressed in g/100 g.

The Results of Unsaturated Fatty Acid in Sturgeon Roes and Enzymolysis Solution are Shown in Table 3.

TABLE 3

Contents of Unsaturated Fatty Acid in Sturgeon Roes and Enzymolysis Solution

| | Content of Ω3 fatty acids/% | Content of Ω6 fatty acids/% | Content of Ω9 fatty acids/% |
|---|---|---|---|
| Sturgeon roes | 1.34 ± 0.12 | 4.64 ± 0.53 | 3.78 ± 0.39 |
| Sturgeon roe enzymolysis solution | 2.62 ± 0.33 | 9.93 ± 0.28 | 8.21 ± 0.77 |

It can be seen from Table 3 that the contents of (23, 26 and 29 fatty acids in the sturgeon roe enzymolysis solution are higher than the content of fatty acid in sturgeon roes. The total content of unsaturated fatty acid per 100 g of enzymolysis solution is more than twice that of sturgeon roes per 100 g.

The protein content, degree of hydrolysis, protein recovery rate, ABTS antioxidant activity and tyrosinase inhibitory activity of the sturgeon roe peptide are evaluated. It is selected that the enzyme addition amount is 1% (according to substrate mass), enzymolysis time is 8 h, and the solid-liquid ratio is 1:6, and alkaline protease is selected as the preparation condition of a sturgeon roe peptidyl delivery system.

II. Protective Effect of Enzymolysis Sample on Oxidative Damage of HaCaT Cells 2.1 Selection of Cytotoxicity and Modeling Concentration HaCaT cells at logarithmic growth stage are selected; the cell concentration is adjusted to $1.5 \times 10^4$ cells/mL; and the cells are inoculated into a 96-well plate. The cells are divided into a normal group and sample groups with different concentration gradients. The normal group is given a blank medium and a sturgeon roe extract (protein concentrations are 0.1, 0.3, 0.5, 0.9, 1.3, and 1.7 mg/mL, respectively). Six parallels are set for each concentration and cultured for 24 h. OD values of the groups are measured by CCK-8 method, and relative cell viability is calculated.

Relative cell viability %=$OD_{sample}/OD_{normal} \times 100\%$.

HaCaT cells are inoculated into a 96-well plate with a concentration of $1.5 \times 10^4$ cells per well, with 100 μL per well. The cells are attached to the wall in an incubator at 37° C. and 5% $CO_2$ for 24 h, and the medium is absorbed and discarded. The cells are divided into a normal group and an $H_2O_2$ damage group (0.5, 0.6, 0.7, 0.8, 0.9, 1, 1.1, 1.2, and 1.3 mmol/L). Six compound wells are set in each group and incubated at 37° C. and 5% $CO_2$ for 2 h. OD values of the groups are measured by CCK-8 method, and relative cell viability is calculated.

Relative cell viability %=OD damage/OD normal 1×100%

2.2 Research on the Protective Effect of Samples on HaCaT Cells with $H_2O_2$ Damaged HaCaT cells are inoculated into a 96-well plate with a concentration of $1.5×10^4$ cells per well, with 100 μL per well. The cells are attached to the wall in an incubator at 37° C. and 5% $CO_2$ for 24 h, and the medium is discarded. The cells are divided into a normal group, a model group and a drug administration group. The normal group and the model group are given a blank medium, and the drug administration group is added with samples of different concentration gradients. Six compound wells are set in each group, and incubated at 37° C. and 5% $CO_2$ for 24 h. The supernatant is sucked and discarded. Except that the normal group is added with the blank medium, 900 μmol/L $H_2O_2$ is added to the model group and the drug administration group for 6 h. OD values of the groups are measured by CCK-8 method, and relative cell viability is calculated.

2.3 Apoptosis Detection

HaCaT cells are inoculated into a 6-well plate at a concentration of $6×10^5$ cells per well, and attached to the wall in an incubator at 37° C. and 5% $CO_2$ for 24 h. The medium is discarded. The cells are divided into a normal group, a model group and a drug administration group. The normal group and the model group are given a blank medium, and samples of different concentration gradients are added to the drug administration group. The cells are incubated at 37° C. and 5% $CO_2$ for 24 h, and the supernatant is absorbed and discarded. Except that the blank medium is added to the normal group, 900 μmol/L $H_2O_2$ is added to the model group and the drug administration group for 6 h. The cells are scraped off with a cell scraper and broken for later use.

$1.0×10^6$ cells are transferred into a 5 mL flow test tube, and centrifuged at 300 g at room temperature for 5 min. The centrifuge liquid is removed; 2 mL of binding buffer is added, and centrifuged at 300 g at room temperature for 5 min. The supernatant is removed. 100 μL of stain buffer resuspension cells are added, and 5 μL of Annexin V APC and 5 μL of PI solution are added, and incubated at room temperature for 25 min. 100 μL of stain buffer is added and tested on the computer.

2.4 Detection of Oxidative Stress Index

The cell treatment mode is consistent with "2.3 cell apoptosis detection". The cells are scraped off with a cell scraper and broken for later use. The indexes are detected by operation according to the relevant steps of kits GSH (glutathione), SOD (superoxide dismutase), MDA (malondialdehyde) and LDH (lactate dehydrogenase).

2.5 Cell Scratch Experiment

HaCaT Human Immortalized Epidermal Cells (HDF Human Dermal Fibroblast cells are inoculated by $1×10^6$ per well) are inoculated by $1.2×10^6$ per well. After the cells are attached to the wall, straight lines are drawn in a 6-well plate with a 200 μL gun head. The cells are divided into a normal group and a sturgeon roe extract (protein concentration) by 0.4 mg/mL. The normal group is added with a basic medium. A sample adding group is added with a sample solution configured by the basic medium. Cell growth conditions are observed at 0 h, 12 h and 24 h respectively.

2.6 Detection of Type I Collagen and Hyaluronic Acid

HaCaT Human Immortalized Epidermal Cells and HDF Human Dermal Fibroblast cells are inoculated on a 12-well plate at $3×10^5$ per well, and attached to the wall for 24 h. Then, a normal medium/sample is added (two concentration gradients are set). After 24 h of culture, the culture supernatant is collected for detection (Human hyaluronic acid (HA) ELISA kit from Nanjing Jiancheng, and human Type I collagen (Col I) ELISA kit).

Figure 13:
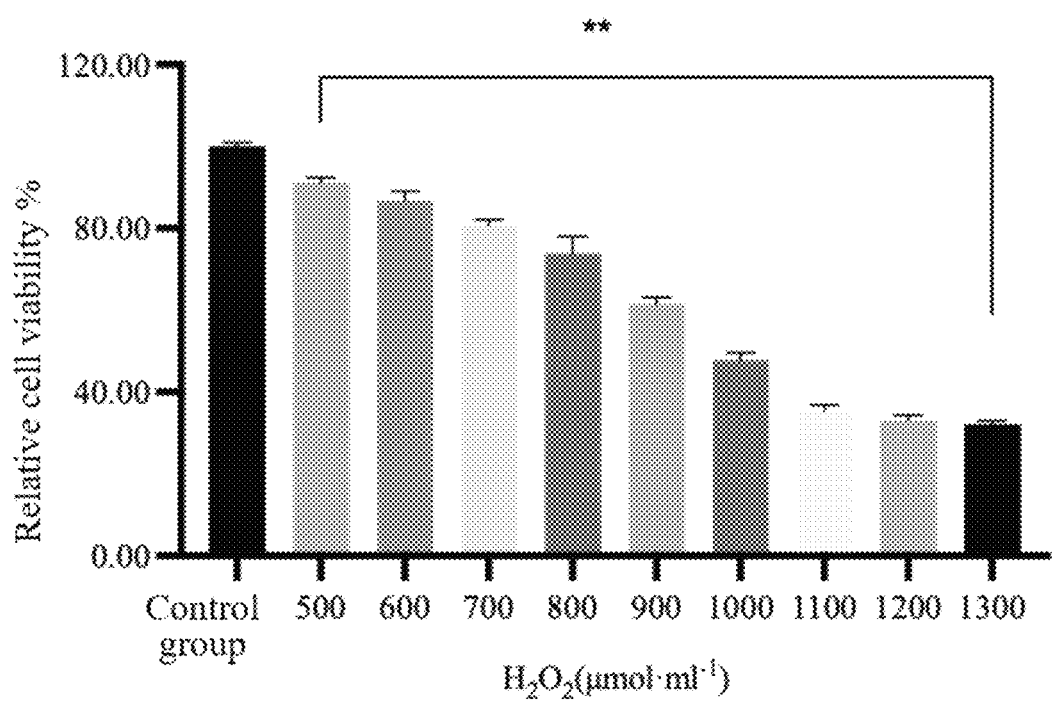
FIG. 13 shows the selection of a molding concentration.

2.7 Experimental Results and Discussion 2.7.1 Selection of Molding Concentration The screening of the molding concentration is shown in FIG. 13.

It can be seen from FIG. 13 that when the molding concentration is selected, if a cell survival rate is too high, the damage is not obvious, and if the survival rate is too low, the cells may have serious irreversible damage, which is not conducive to later experiments. A concentration between 50% and 70% of cell viability should be selected as the molding concentration. When the concentration of $H_2O_2$ reaches 900 μmol/mL, an inhibition rate is 62%. Therefore, 900 μmol/mL $H_2O_2$ is selected in this experiment to construct a cell oxidative stress model to act for 6 h, and a HaCaT cell oxidative damage model is established.

Figure 14:
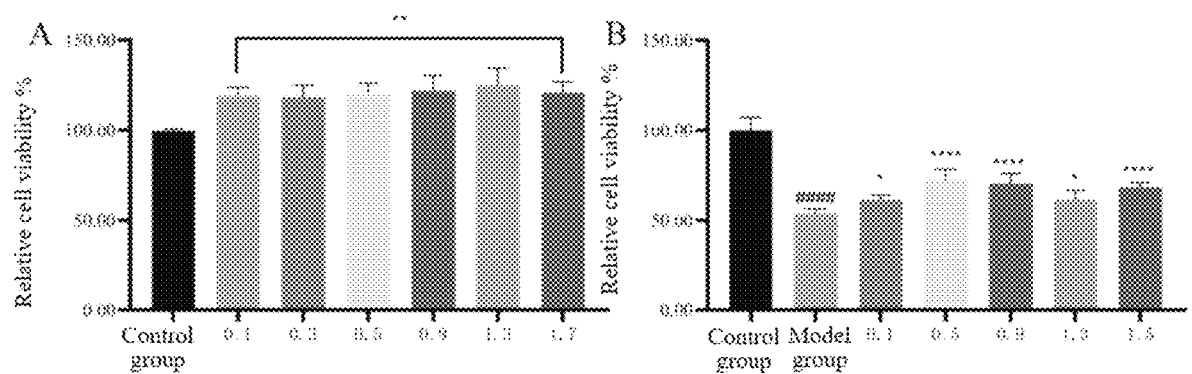
FIG. 14A shows the proliferative effect of sturgeon roe extract protein concentration on HaCaT cells.
FIG. 14B also demonstrates the protective effect of sturgeon roe extract protein concentration on HaCaT cells damaged by $H_2O_2$.

2.7.2 Research on Protective Effect of Enzymolysis Product of Sturgeon Roes on HaCaT Cells with $H_2O_2$ Damage Results are shown in FIG. 14.

Wherein the cytotoxicity of the enzymatic hydrolysate of sturgeon is shown by A in FIG. 14.

It can be seen from A in FIG. 14 that the sturgeon roe extract can promote the proliferation of HaCaT cells when the protein concentration of the sturgeon roe extract is 0.1-1.7 mg/mL, and the sturgeon roe extract has no toxic effect on HaCaT cells within this range.

The protective effect of the enzymolysis product of sturgeon roes on HaCaT cells with $H_2O_2$ damage is shown by B in FIG. 14.

It can be seen from B in FIG. 14 that the sturgeon roe extract has a significant protective effect (P<0.05) on HaCaT cells with $H_2O_2$ damage when the protein concentrations are 0.1, 0.3, 0.5, 0.9, 1.3 and 1.7 mg/mL, and has an extremely significant protective effect (P<0.01) when the protein concentrations of the sturgeon roe extract are 0.5, 0.9 and 1.5 mg/mL.

Figure 15:
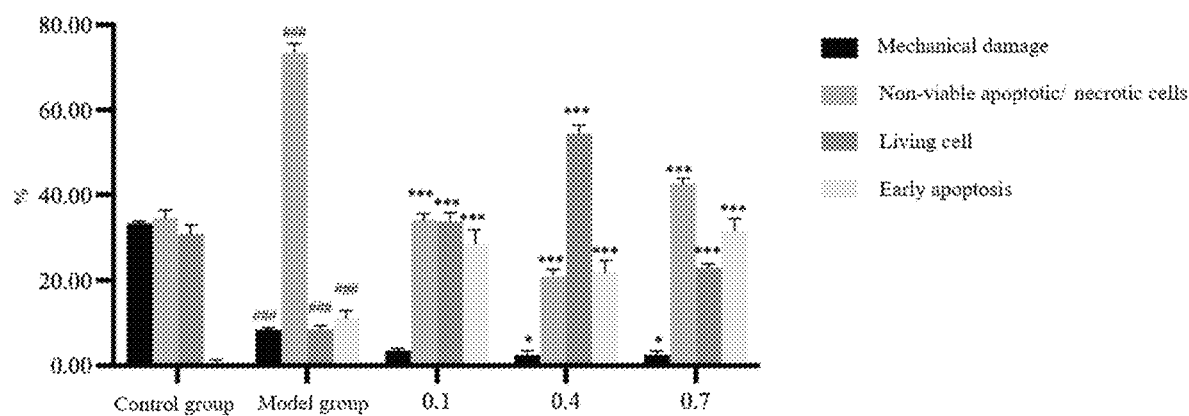
FIG. 15 shows the protective effect of samples on HaCaT cells damaged by $H_2O_2$ by a flow cytometer.

2.7.3 Protective Effect of Samples on HaCaT Cells with $H_2O_2$ Damage by Flow Cytometer Results are shown in Table 4 and FIG. 15.

TABLE 4

Protective Effect of Samples on HaCaT Cells with $H_2O_2$ Damage by Flow Cytometer

| Sample | Q2-1% (mechanical damage) | Q2-2% (late apoptosis) | Q2-3% living cell | Q2-4% (early apoptosis) | Early + late apoptosis |
|---|---|---|---|---|---|
| Normal group | 33.91% | 35.13% | 30.15% | 0.81% | 35.94% |
| Model group | 8.66% | 71.52% | 8.45% | 11.37% | 82.89% |
| Sturgeon 0.1 | 3.09% | 33.42% | 32.07% | 31.42% | 64.84% |
| Sturgeon 0.4 | 1.38% | 19.80% | 53.89% | 24.93% | 44.73% |
| Sturgeon 0.9 | 2.20% | 42.78% | 22.88% | 32.14% | 74.92% |

It can be seen from Table 4 that different quadrants of the flow cytometer represent different cell states.

It can be seen from FIG. 15 that in the experiment of protecting HaCaT cells from $H_2O_2$ damage by sturgeon, non-viable apoptotic cells in the model group are significantly higher than those in the control group, and the viable count in the model group is significantly lower than that in the control group (P<0.05). When the protein content of the enzymatic hydrolysate of the sturgeon is 0.1, 0.4 and 0.7 mg/mL, the non-viable apoptotic cells are significantly lower than those in the model group (P<0.05) and the living cells are significantly higher than those in the model group, with the best effect at 0.4 mg/mL.

Figure 16:
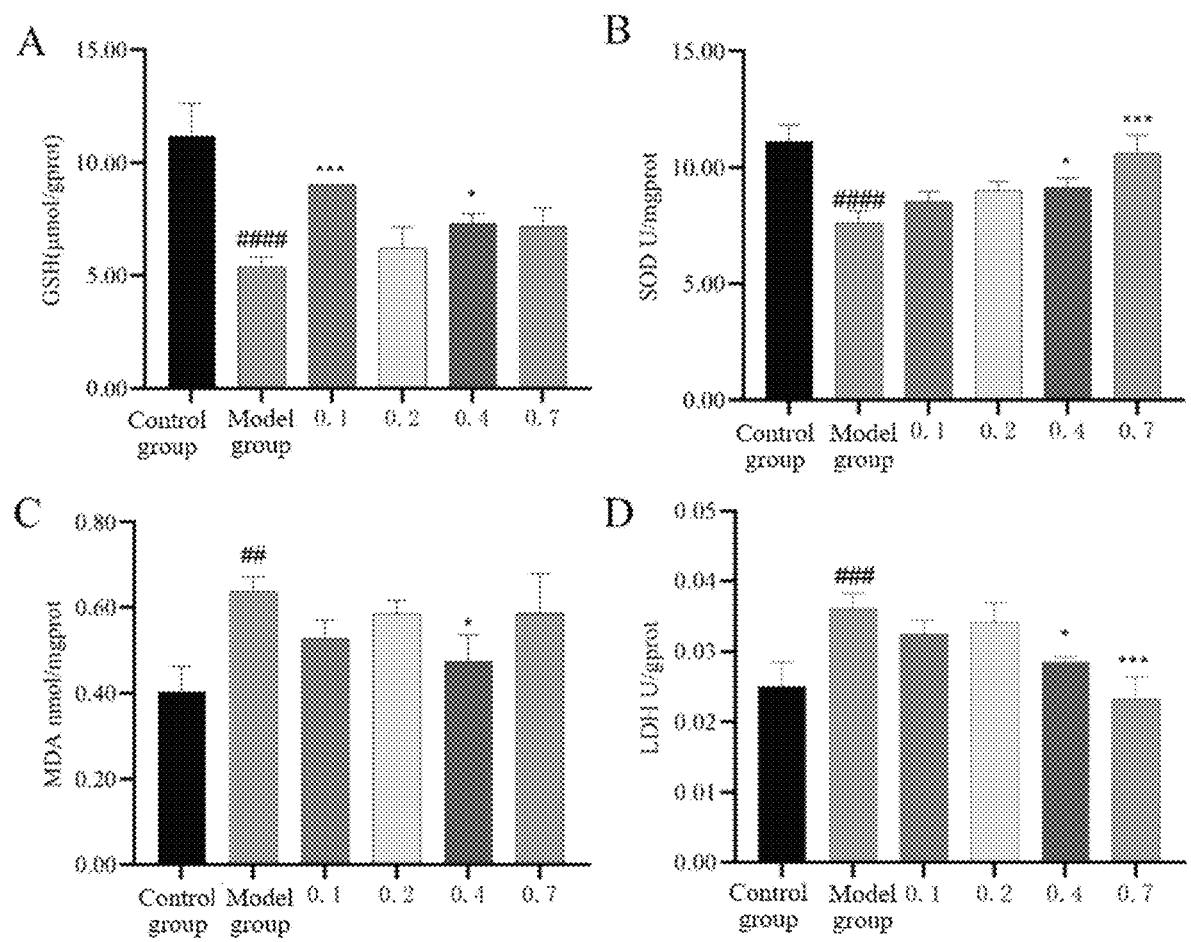
FIG. 16A shows the effect of sturgeon enzymatic hydrolysate on glutathione (GSH) levels in damaged cells.
FIG. 16B shows the effect of sturgeon enzymatic hydrolysate on superoxide dismutase (SOD) in damaged cells.
FIG. 16C shows the effect of sturgeon enzymatic hydrolysate on malondialdehyde (MDA) levels in damaged cells.

2.7.4 Effect of Enzymolysis Product of Sturgeon Roes on Oxidative Stress Level of Damaged Cells Results are shown in FIG. 16.

(1) Effect of Enzymolysis Product of Sturgeon Roes on Glutathione (GSH) Level of Damaged Cells GSH is a coenzyme of many enzymes such as GSH-Px, which is involved in scavenging HO, $O^{2-}$, $H_2O_2$, etc., and capable of effectively protecting the body from oxidative stress damage. Therefore, the amount of GSH can reflect the antioxidant capacity of the body to a certain extent.

The effect of enzymatic hydrolysate of sturgeon on glutathione (GSH) level of damaged cells is shown by A in FIG. 16.

It can be seen from A in FIG. 16 that GSH content in the model group is significantly lower than that in the control group (P<0.05), and GSH content in the sample group is increased to varying degrees, wherein the GSH content is highest when the protein concentration of the sturgeon extract is 0.1 mg/mL, which indicates that the fish roe extract can improve the oxidative stress ability of cells by increasing the GSH content.

(2) Effect of Enzymolysis Product of Sturgeon Roes on Superoxide Dismutase (SOD) in Damaged Cells SOD can convert harmful superoxide free radicals into $H_2O_2$ through cell respiration. Cell damage can lead to the change of the oxidative stress level. In order to further explore the reasons, the project team detects the activity of superoxide dismutase SOD in cells.

The effect of enzymatic hydrolysate of sturgeon on superoxide dismutase (SOD) of damaged cells is shown by B in FIG. 16.

It can be seen by B in FIG. 16 that the SOD activity of the model group is significantly decreased compared with the control group, while compared with the model group, the sturgeon roe extract can significantly increase the SOD activity of cells (P<0.05), and the SOD activity is gradually increased with the increase of sample concentration. Wherein the sturgeon roe extract with the protein concentration of 0.7 mg/mL has the strongest ability to improve the SOD activity.

The results show that the sturgeon roe extract can achieve the purpose of improving the oxidative stress state of cells by improving the SOD activity.

(3) Effect of Enzymolysis Product of Sturgeon Roes on Malondialdehyde (MDA) in Damaged Cells Malondialdehyde (MDA) is one of the iconic products of lipid peroxidation, and the content of MDA in the organism can directly reflect the degree of oxidation or damage of the organism. Therefore, improving the MDA level of the body is also one of the important means to achieve oxidation resistance and maintain cell vitality.

The effect of enzymatic hydrolysate of sturgeon on malondialdehyde (MDA) in damaged cells is shown by C in FIG. 16.

It can be seen from C in FIG. 16 that compared with the normal group, MDA content in the model group is significantly increased (P<0.001), and MDA content is significantly decreased (P<0.05) with the treatment of the sample group of the sturgeon roe extract, wherein the sturgeon roe extract with the protein concentration of 0.4 mg/mL has the strongest ability to reduce MDA.

(4) Effect of Enzymolysis Product of Sturgeon Roes on Lactate Dehydrogenase (LDH) in Damaged Cells The damage of the cell membrane structure caused by apoptosis or necrosis results in the release of enzymes in the cytoplasm into a culture solution, including lactate dehydrogenase (LDH) which has stable enzyme activity. Quantitative analysis of cytotoxicity can be achieved by detecting LDH activity.

The effect of enzymatic hydrolysate of the sturgeon on lactate dehydrogenase (LDH) in damaged cells is shown by D in FIG. 16.

It can be seen from D in FIG. 16 that LDH content in the supernatant of the cell culture solution of the model group is significantly increased, and LDH content in the cell supernatant is decreased with the increase of sample concentration. LDH content of the sturgeon roe extract is significantly lower than that of the model group when the protein concentration is 0.4 mg/mL (P<0.05). When the protein concentration of the sturgeon roe extract is 0.7 mg/mL, the LDH content is the lowest and the effect is the best.

Based on the above experimental results, the protein concentration 0.4 mg/mL of the sturgeon roe extract is selected for a cell scratch experiment.

2.7.5 Cell Scratch Experiment

HDF cells are the abbreviation of Human Dermal Fibroblast cells. This is a cell type that exists in the dermis of human skin and is mainly responsible for synthesizing collagen, elastic fibers and other extracellular matrix molecules and maintaining the structure, elasticity and stability of the skin. HDF cells play an important role in physiological and pathological processes such as skin healing, wound repair and skin aging. Because of their key role in skin health and diseases, HDF cells are often used by researchers to explore cell biology, molecular mechanisms, and the pathogenesis of related diseases.

HaCaT cells belong to a human skin epithelial cell line, also known as Human Keratinocyte Cells (HaCaT). The cell line is isolated and cultured from a normal human skin keratosis. HaCaT cells have high proliferative activity in culture in vitro and can constantly divide to form multi-layer cell accumulation, similar to the epidermal layer of human skin. Because of the characteristic of the HaCaT cells to simulate skin epithelial cells, the HaCaT cells are often used in skin biology research, such as cell proliferation, differentiation, keratinization and skin diseases. The HaCaT cells can also be widely used in drug safety evaluation, cosmetic testing, and biomedical research to explore the molecular mechanisms of skin health and diseases.

Figure 17:
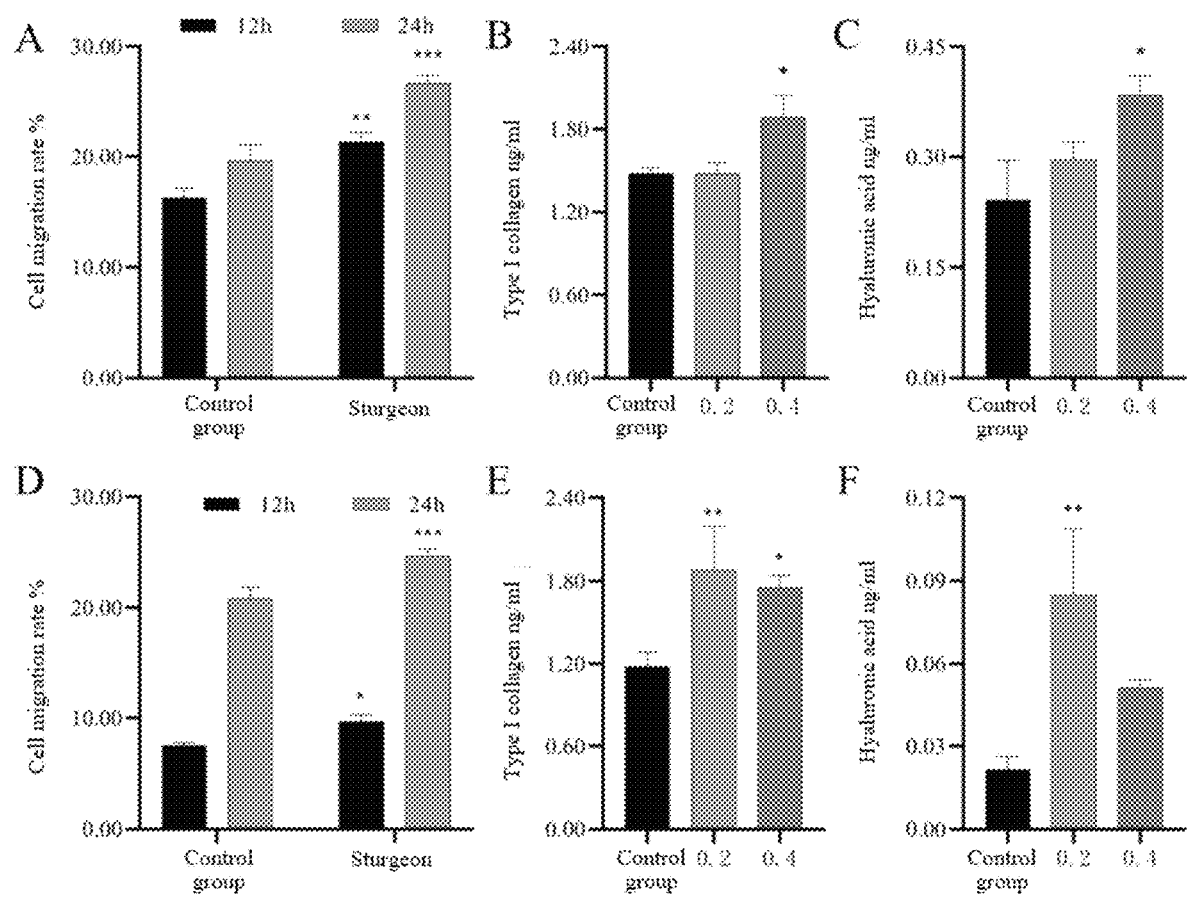
FIG. 17A shows the effect of sturgeon roe extract on the migration speed of HaCaT cells.
FIG. 17B shows the effect of sturgeon roe extract on the content of type I collagen in HaCaT cells.
FIG. 17C shows the effect of sturgeon roe extract on hyaluronic acid in HaCaT cells.
FIG. 17D shows the effect of sturgeon roe extract on the migration speed of HDF cells.
FIG. 17E shows the effect of sturgeon roe extract on the content of type I collagen in HDF cells.
FIG. 17F shows the effect of sturgeon roe extract on hyaluronic acid in HDF cells.

Results are shown in FIG. 17. Wherein the effect of the sturgeon roe extract on the migration rate of the HaCaT cells is shown by A in FIG. 17; the effect of the sturgeon roe extract on the type I collagen content of the HaCaT cells is shown by B in FIG. 17; the effect of the sturgeon roe extract on hyaluronic acid of the HaCaT cells is shown by C in FIG. 17; the effect of the sturgeon roe extract on the migration rate of HDF cells is shown by D in FIG. 17; the effect of the sturgeon roe extract on type I collagen content of HDF cells is shown by E in FIG. 17; and the effect of the sturgeon roe extract on hyaluronic acid of HDF cells is shown by F in FIG. 17.

(1) Effect of Sturgeon Roe Extract on Migration Rate of HaCaT and HDF Cells

It can be seen from A in FIG. 17 and D in FIG. 17 that compared with the control group, sturgeon samples can significantly promote scratch healing at 0-12 h and 12-24 h (P<0.05), and increase the migration rates of HaCaT and HDF cells.

(2) Effect of Enzymolysis Product of Sturgeon Roes on Content of Type I Collagen It can be seen from B in FIG. 17 that the HaCaT cells cultured from sturgeon samples show a dosage-dependent trend within a specified concentration. When the protein concentration of the sturgeon roe extract is 0.4 mg/mL, the content of type I collagen secreted by the cells can be significantly increased ($P<0.05$).

It can be seen from E in FIG. 17 that HDF cells cultured from sturgeon samples can promote the production of type I collagen within concentrations. When the protein concentration of the sturgeon roe extract is 0.2 mg/mL, the content of type I collagen secreted by cells can be significantly increased ($P<0.01$).

(3) Effect of Enzymolysis Product of Sturgeon Roes on the Content of Hyaluronic Acid It can be seen from C in FIG. 17 that all the sample concentrations can increase the content of hyaluronic acid in the HaCaT cells. With the increase of the protein concentration of the sturgeon roe extract, the content of hyaluronic acid in the cells is increased and dosage-dependent at 0.2-0.4 mg/mL.

It can be seen from F in FIG. 17 that all the sample concentrations can increase the content of hyaluronic acid in the HDF cells, and the content of hyaluronic acid in the cells can be significantly increased ($P<0.001$) when the protein concentration of the sturgeon roe extract is 0.2 mg/mL, and the content of hyaluronic acid in the cells can be significantly increased ($P<0.05$) when the protein concentration of the sturgeon roe extract is 0.4 mg/mL.

III. Sequence Identification and Virtual Screening of Bioactive Polypeptide 3.1 Sequence Identification of Bioactive Polypeptide in Enzymolysis Product The samples are analyzed by LC-MS/MS equipped with an online nanojet ion source. 3 μL of samples are loaded, and the samples are separated with a gradient of 60 min. The column flow rate is controlled at 300 nL/min, the column temperature is 40° C., and the electrospray voltage is 2 kV. The gradient starts from 2% B-phase, rises to 35% with a nonlinear gradient in 47 min, and rises to 100% within 1 min for 12 min.

A mass spectrometer is operated in a data-dependent collection mode, and automatically switched between MS and MS/MS collection. Mass spectrum parameters are set as follows: (1) MS: scanning range (m/z): 200-2000; resolution: 70,000; AGC target: 3e6; maximum injection time: 50 ms; (2) HCD-MS/MS: resolution: 17,500; AGC target: 1e5; maximum injection time: 45 ms; collision energy: 28%; and dynamic exclusion time: 30 s.

Setting of database search parameters: a tandem mass spectrometry is analyzed by PEAKS Studio version 10.6. PEAKS DB searches a database for uniprot-Salmo salar or uniprot-*Acipenser sinensis* and sets none enzymolysis. An allowable error of fragment ion mass of database search parameters is 0.02 Da, and an allowable error of parent ion mass is 7 ppm. The protein calorie value is 1 unique peptide. The peptide caloric value is −101 gP>20.

3.2 Virtual Screening of Active Peptide

The database of bioactive peptide and a computer virtual screening tool are used to analyze, virtually screen and predict the potential bioactive peptide in the peptide sequence of the enzymolysis product.

The distribution of all target polypeptide sequences obtained by the mass spectrometer is shown by using Upset Venn diagram.

The potential biological activity of peptide fragments is predicted and ranked by Peptide Ranker, and cell permeability is predicted and ranked by CPPpred, which can evaluate the cell penetration potential of peptide. Both scores are between 0 and 1. The higher the score is, the greater the potential is.

The peak area of the peptide represents the content to some extent, and thus can be used as a filtering condition to improve the accuracy of the identified peptide fragment and screen the major contributor peptide fragment. Therefore, the potential bioactive peptide is screened by taking the filtering conditions of Peptide Ranker score >0.5, CPPpred score >0.1, and relative peak area >0.05%. A bubble diagram is made by taking the Peptide Ranker score as an x-axis, the CPPpred score as a y-axis, and the peak area of the peptide as the area of a circle, to show a relationship among the three.

There is a relationship between protein function, charge and hydrophobicity, and net charge and hydrophobicity can be used for describing the intermolecular force of protein. Some researches have found that protein hydrophobicity is significantly correlated with emulsification properties and solubility. Therefore, PepDraw is used for determining the chemical properties of polypeptide: isoelectric point, net charge and hydrophobicity.

3.3 Results and Discussion 3.3.1 Analysis of Polypeptide from Enzymolysis Product of Sturgeon Roes The potential bioactive peptides in enzymolysis products of sturgeon roes are screened by mass spectrometry and virtual screening means and in combination with the indexes of peptide ranker, peak area and CPPpred prediction.

Figure 18:
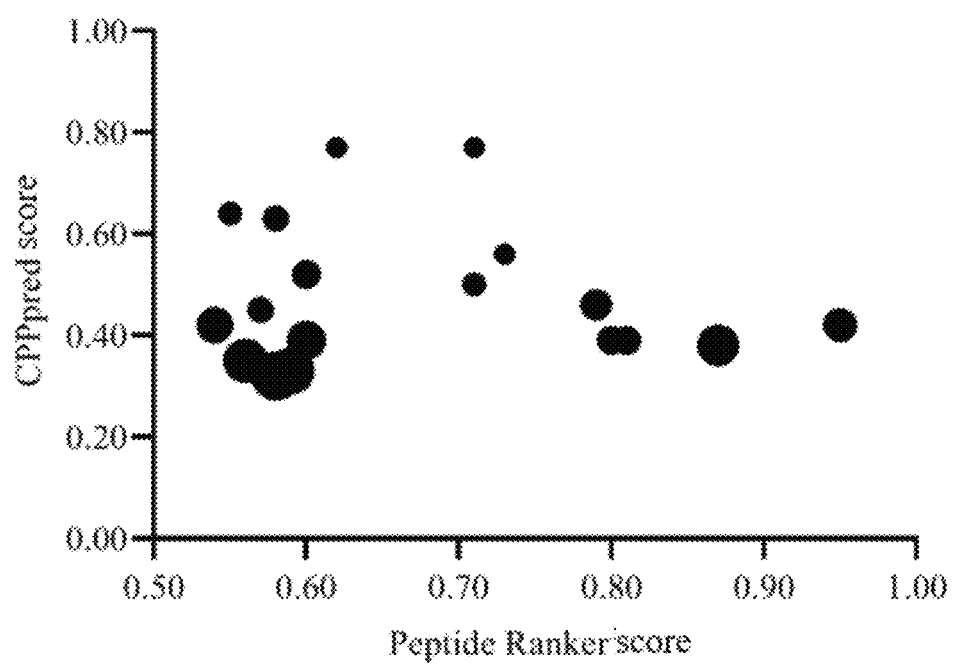
FIG. 18 shows scores of polypeptide activity.

Results are shown in Table 5 and FIG. 18.

TABLE 5

| | Peptide Fragments of Sturgeon | | | | | | |
|---|---|---|---|---|---|---|---|
| Peptide sequence | Peptide Ranker score | Molecular weight (Da) | CPPpred score | Relative peak area (%) | Hydro-phobicity (kcal/mol) | Iso-electric point | Net charge |
| LGR | 0.62 | 344.22 | 0.77 | 0.11 | 9.61 | 10.73 | 1 |
| GLR | 0.71 | 344.22 | 0.77 | 0.11 | 9.61 | 10.73 | 1 |
| RLY | 0.55 | 450.26 | 0.64 | 0.05 | 7.75 | 9.64 | 1 |
| LLLP (SEQ ID NO: 1) | 0.58 | 454.32 | 0.63 | 0.17 | 4.29 | 5.63 | 0 |
| LPL | 0.73 | 341.23 | 0.56 | 0.11 | 5.54 | 5.58 | 0 |
| ALLP (SEQ ID NO: 2) | 0.6 | 412.27 | 0.52 | 0.08 | 6.04 | 5.65 | 0 |
| LKFL (SEQ ID NO: 3) | 0.71 | 519.34 | 0.5 | 0.05 | 6.49 | 10.14 | 1 |
| TGLW (SEQ ID NO: 4) | 0.79 | 475.24 | 0.46 | 0.06 | 5.96 | 5.33 | 0 |
| LQPL (SEQ ID NO: 5) | 0.57 | 469.29 | 0.45 | 0.17 | 6.31 | 5.58 | 0 |
| RLPF (SEQ ID NO: 6) | 0.95 | 531.32 | 0.42 | 0.07 | 6.89 | 10.9 | 1 |
| AVLGPL (SEQ ID NO: 7) | 0.54 | 568.36 | 0.42 | 0.14 | 6.73 | 5.6 | 0 |

TABLE 5-continued

Peptide Fragments of Sturgeon

| Peptide sequence | Peptide Ranker score | Molecular weight (Da) | CPPpred score | Relative peak area (%) | Hydro-phobicity (kcal/mol) | Iso-electric point | Net charge |
|---|---|---|---|---|---|---|---|
| LGPL (SEQ ID NO: 8) | 0.8 | 398.25 | 0.39 | 0.08 | 6.69 | 5.58 | 0 |
| NLPL (SEQ ID NO: 9) | 0.6 | 455.27 | 0.39 | 0.47 | 6.39 | 5.41 | 0 |
| GLPL (SEQ ID NO: 10) | 0.81 | 398.25 | 0.39 | 0.08 | 6.69 | 5.6 | 0 |
| WSLL (SEQ ID NO: 11) | 0.87 | 517.29 | 0.38 | 0.16 | 3.77 | 5.69 | 0 |
| ALPLDPK (SEQ ID NO: 12) | 0.56 | 752.44 | 0.35 | 0.12 | 12.62 | 6.44 | 0 |
| KYPL (SEQ ID NO: 13) | 0.59 | 519.31 | 0.33 | 0.09 | 8.88 | 9.78 | 1 |
| VDNHVPLRL (SEQ ID NO: 14) | 0.58 | 1061.6 | 0.32 | 0.15 | 13.25 | 7.89 | 0 |

It can be seen from Table 5 that 18 polypeptide sequences with potential biological activity are obtained from the enzymolysis products of sturgeon roes in this research. In combination with related data such as polypeptide activity score in FIG. 18, sturgeon roe peptide NLPL (SEQ ID NO: 9) is further selected for subsequent animal experiments and metabolic experiment research.

IV. Animal Experimental Research of the Repair Effect of Samples on Aging Mice 4.1 Research of the Improvement Effect of Samples on D-Galactose Induced Aging Mice 4.1.1 Molding and Intervention In this research, C57BL/6J mice are selected for experiments and divided into 8 groups: a normal group, a model group, a low-dosage sample group, a high-dosage sample group, two pure peptide sample groups and two control groups, with 5 mice in each group. Except the normal group, mice in the sample groups and the model group are injected with 5% D-galactose solution (125 mg/kg) subcutaneously at the neck and back daily at the beginning of the experiment to establish an aging model, which lasts for 8 weeks. The normal group and the control groups receive the same amount of saline injection. Starting from the 8th day of modeling, mice in the sample groups receive the corresponding intragastric sample treatment for 7 weeks. The control groups and the model group continuously receive constant normal saline intragastric administration with the same volume. During the experiment, all the mice are fed with an ordinary feed in an environment of 20-24° C. and operated according to specific dosage indexes.

The specific dosage information is shown in Table 6.

TABLE 6

Dosage Setting for Animal Experiment

| Sample | Dosage mg/kg bw | Mg/60 kg |
|---|---|---|
| Sturgeon polypeptide-L | 37.5 | 250 |
| Sturgeon polypeptide-H | 75 | 500 |
| Sturgeon NLPL (SEQ ID NO: 9) | 75 | 500 |

4.1.2 Index Determination

To evaluate oxidative stress-related indexes, after 1 h from final drug administration, the mice are subjected to intraperitoneal anesthesia with 3% pentobarbital sodium (30 mg/kg body weight), and then subjected to blood sampling through the orbital venous plexus of the mice. The obtained blood is stored in a standard blood sampling tube at room temperature for 1.5 h. Subsequently, the blood is centrifuged at 3000 rpm for 10 min and the supernatant is taken. According to the instructions of the kit, the supernatant is used for determining the activity of superoxide dismutase (SOD), glutathione (GSH) and glutathione peroxidase (GSH-Px) and the content of malondialdehyde (MDA).

In addition, to determine the biochemical indexes related to the skin, a skin tissue sample is taken from the back hair removal area of the mice and the subcutaneous tissue below it is ensured to be excised, for sampling by about 0.1 g. The tissue sample is rinsed twice in pre-cooled normal saline and then drained for the surface moisture with filter paper. Next, the tissue is placed into a 4 mL EP tube and cut into smaller fragments. Under ice bath conditions, the pre-cooled normal saline (with a final tissue concentration of 0.1 g/mL) is added to these tissue fragments and the tissue fragments are homogenized. Then, the tissue fragments are centrifuged at 12000 rpm for 20 min to obtain the supernatants. Finally, the contents of collagen and hyaluronic acid (HA) are determined by using these supernatants according to the steps of the kit.

4.2 Research on Blood Metabolism of Target Polypeptide 4.2.1 Animal Intragastric Administration In this research, SD rats are used and divided into three groups: a normal group and sturgeon NLPL (SEQ ID NO: 9) groups (50 mg/kg bw of daily dosage). At 12 h before the experiment, the rats are fasted but allowed to drink water. At 15 min, 45 min, 90 min, 180 min and 360 min after intragastric administration, all rats are anesthetized with 3% pentobarbital sodium, subjected to blood sampling through the abdominal aorta, and then euthanized. The polypeptide samples are prepared by solid phase synthesis and desalted.

4.2.2 Polypeptide Detection 4.2.2.1 Sample Pretreatment
  (1) The required samples are taken out, thawed, and mixed uniformly by vortex.
  (2) 40 μL of sample is taken from the mixed sample, added with 120 μL of methanol, then shaken for 10 min, and centrifuged at low temperature for 10 min.
  (3) 70 μL of supernatant is taken out from the centrifuged sample for subsequent determination.

4.2.2.2 Preparation of Standard Solution

The standard concentration is shown in Table 7.

TABLE 7

Standard Concentration (unit: ng/mL)

| | SD1 | SD2 | SD3 | SD4 | SD5 | SD6 | SD7 |
|---|---|---|---|---|---|---|---|
| Polypeptide | 0.1 | 0.5 | 1 | 2 | 5 | 10 | 20 |

4.2.2.3 LC-MS/MS Detection

Chromatographic separation is performed by using Waters ACQUITY UPLC I-CLASS ultra-high performance liquid chromatography equipment. Specific conditions are as follows: chromatographic column: Waters UPLC HSS T3 (1.8 μm, 2.1 mm×100 mm)—mobile phase: phase A (water, 0.1% formic acid), phase B (methanol)—flow rate: 0.3 mL/min-injection volume: 5.0 μL-column temperature: 40° C.—single sample analysis time: 8 min.

The gradient procedure of the mobile phase is shown in Table 8.

TABLE 8

Gradient Procedure of Mobile Phase

| Time (min) | Phase A (v %) | Phase B (v %) |
| --- | --- | --- |
| 0 | 90 | 10 |
| 1 | 90 | 10 |
| 6 | 0 | 100 |
| 6.1 | 90 | 10 |
| 8 | 90 | 10 |

Mass spectrometric detection is performed by using Waters XEVO TQ-XS series four-pole mass spectrometer. Specific conditions are as follows: positive ion source voltage: 3.0 kV-cone well voltage: 30 V-solvent removal temperature: 500° C.—solvent removal gas flow rate: 1000 L/h-cone well gas flow rate: 150 L/h.

4.3 Data Processing

Data are expressed in the form of Mean±SD. Data processing and significance analysis are performed by Graphpad. $P<0.05$ and $P<0.01$ indicate significant difference and extremely significant difference in data. The target peak area in the polypeptide metabolism data is calculated by using TargetLynx software, and an allowable error of retention time is 15 s. The calculation of concentration is based on a standard curve method to obtain quantitative results.

Figure 19:
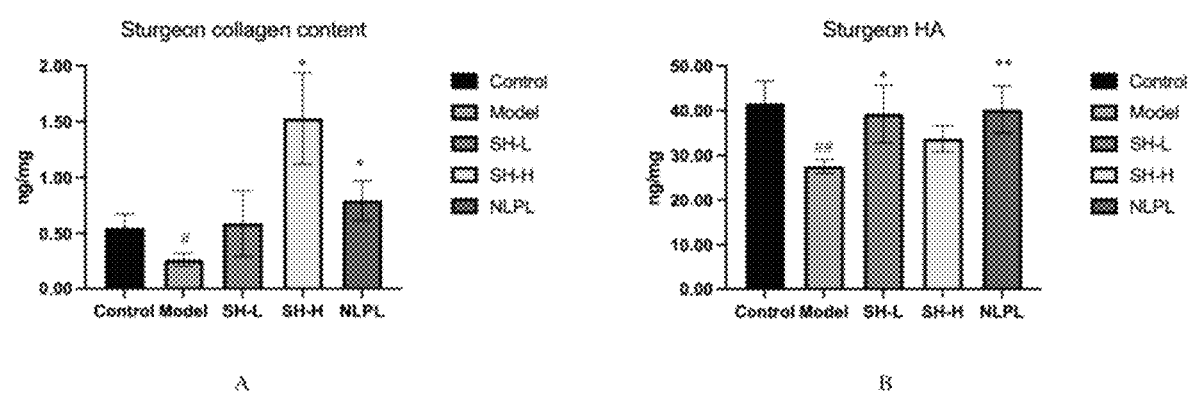
FIG. 19A shows the effect of sturgeon enzymatic hydrolysates on collagen content in the skin of aged mice.
FIG. 19B shows the effect of sturgeon enzymatic hydrolysates on hyaluronic acid content in the skin of aged mice.

4.4 Results and Discussion 4.4.1 Research of Anti-Aging Effect of Enzymolysis Products of Sturgeon on Aging Mice 4.4.1.1 Effects of Enzymolysis Products of Sturgeon on Skin Indexes of Aging Mice Results are shown in FIG. 19.

It can be seen from A in FIG. 19 that compared with the normal group, the collagen content in the skin of the model group is significantly decreased ($P<0.05$). Compared with the model group, the enzymolysis products of sturgeon can increase the collagen content in the skin of aging mice, wherein the effects of the high-dosage treatment group and the NLPL (SEQ ID NO: 9) pure peptide group are significant ($P<0.05$).

It can be seen from B in FIG. 19 that compared with the normal group, the content of hyaluronic acid in the skin of the model group is significantly reduced ($P<0.01$). Different treatment groups can increase the content of hyaluronic acid in the skin of aging mice, wherein the low-dosage sturgeon group ($P<0.05$) and the NLPL (SEQ ID NO: 9) group have significant effects ($P<0.01$).

Figure 20:
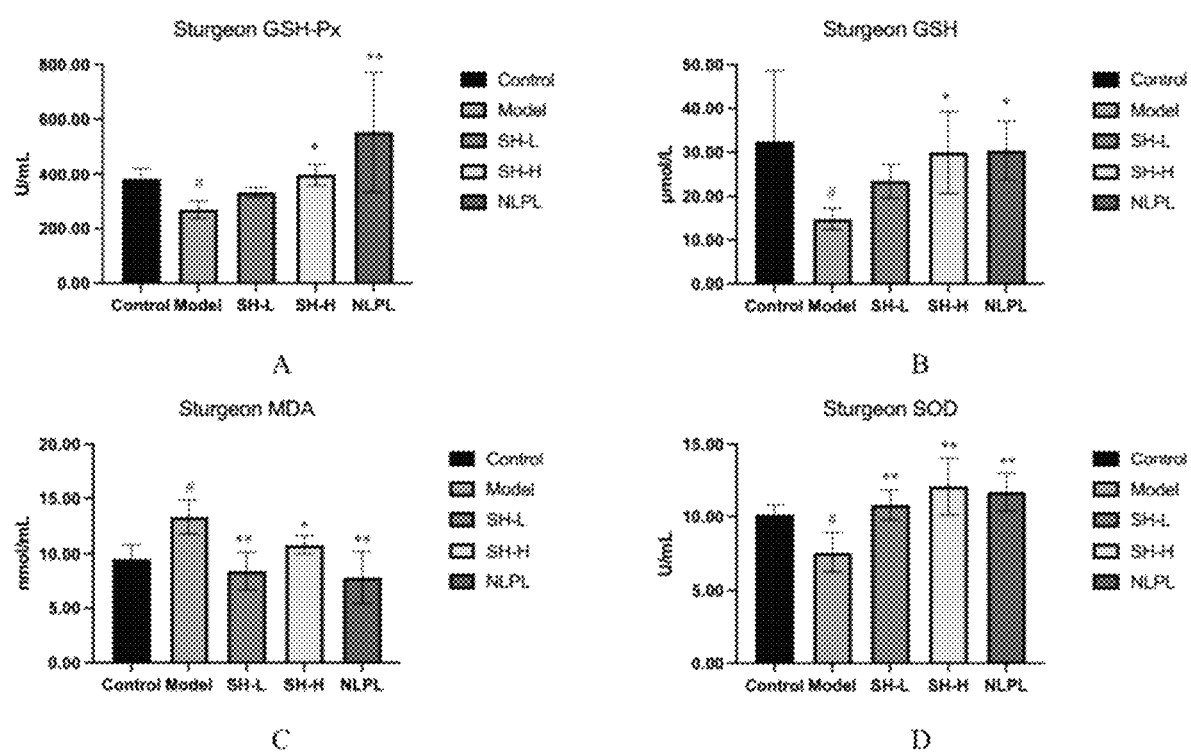
FIG. 20A shows the effect of sturgeon enzymatic hydrolysates on GSH-Px content in the blood of aged mice.
FIG. 20B shows the effect of sturgeon enzymatic hydrolysates on GSH content in the blood of aged mice.
FIG. 20C shows the effect of sturgeon enzymatic hydrolysates on MDA content in the blood of aged mice.
FIG. 20D shows the effect of sturgeon enzymatic hydrolysates on SOD content in the blood of aged mice after D-galactose treatment.

4.4.1.2 Effects of Enzymolysis Products of Sturgeon on Blood Antioxidant Indexes of Aging Mice Results are shown in FIG. 20.

It can be seen from A in FIG. 20 that GSH-Px content in the model group is significantly decreased compared with the normal group, and GSH-Px content in different treatment groups can be increased to a certain extent, wherein the high-dosage group of SH can significantly increase the GSH-Px content ($P<0.05$), and the NLPL (SEQ ID NO: 9) group can extremely significantly increase the GSH-Px content ($P<0.01$). A dosage-dependent trend is presented.

It can be seen from B in FIG. 20 that compared with the normal group, the GSH content in the model group is significantly reduced, and the GSH content in different treatment groups can be increased, wherein the high-dosage group of SH and the NLPL (SEQ ID NO: 9) group have the ability to significantly increase the GSH content ($P<0.05$).

It can be seen from C in FIG. 20 that compared with the normal group, MDA content in the model group is significantly increased, which indicates that D-galactose treatment shows an obvious paper peroxidation phenomenon. Different treatment groups can significantly reduce MDA content, wherein the low-dosage group of SH and the NLPL (SEQ ID NO: 9) have better reducing effects.

It can be seen from D in FIG. 20 that SOD content in D-galactose post-treatment system is significantly reduced, and SOD activity in aging mice can be significantly increased in different treatment groups, or even higher than that of the normal group. This indicates that sturgeon polypeptide has strong SOD activity enhancement effect.

In conclusion, the enzymolysis products of sturgeon and sturgeon polypeptides have excellent effects on improving the oxidative stress level of aging mice.

Figure 21:
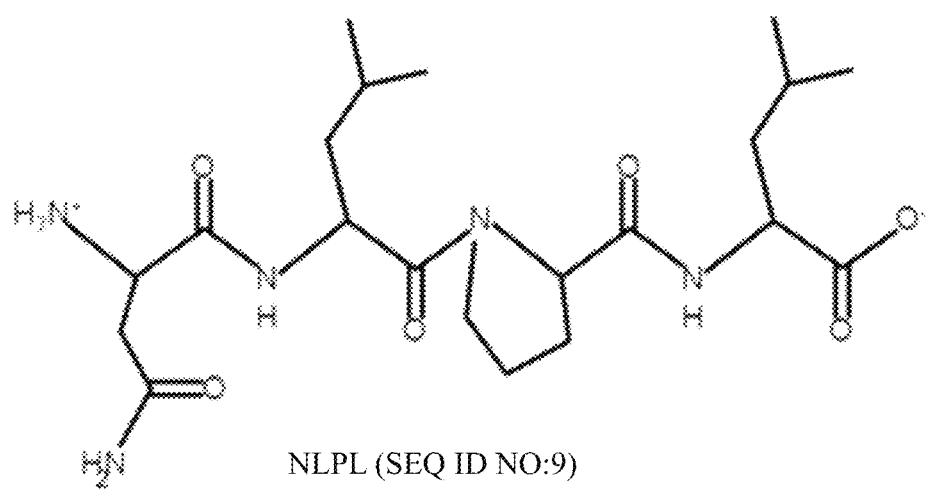
FIG. 21 shows the structure of a polypeptide standard.
Figure 22:
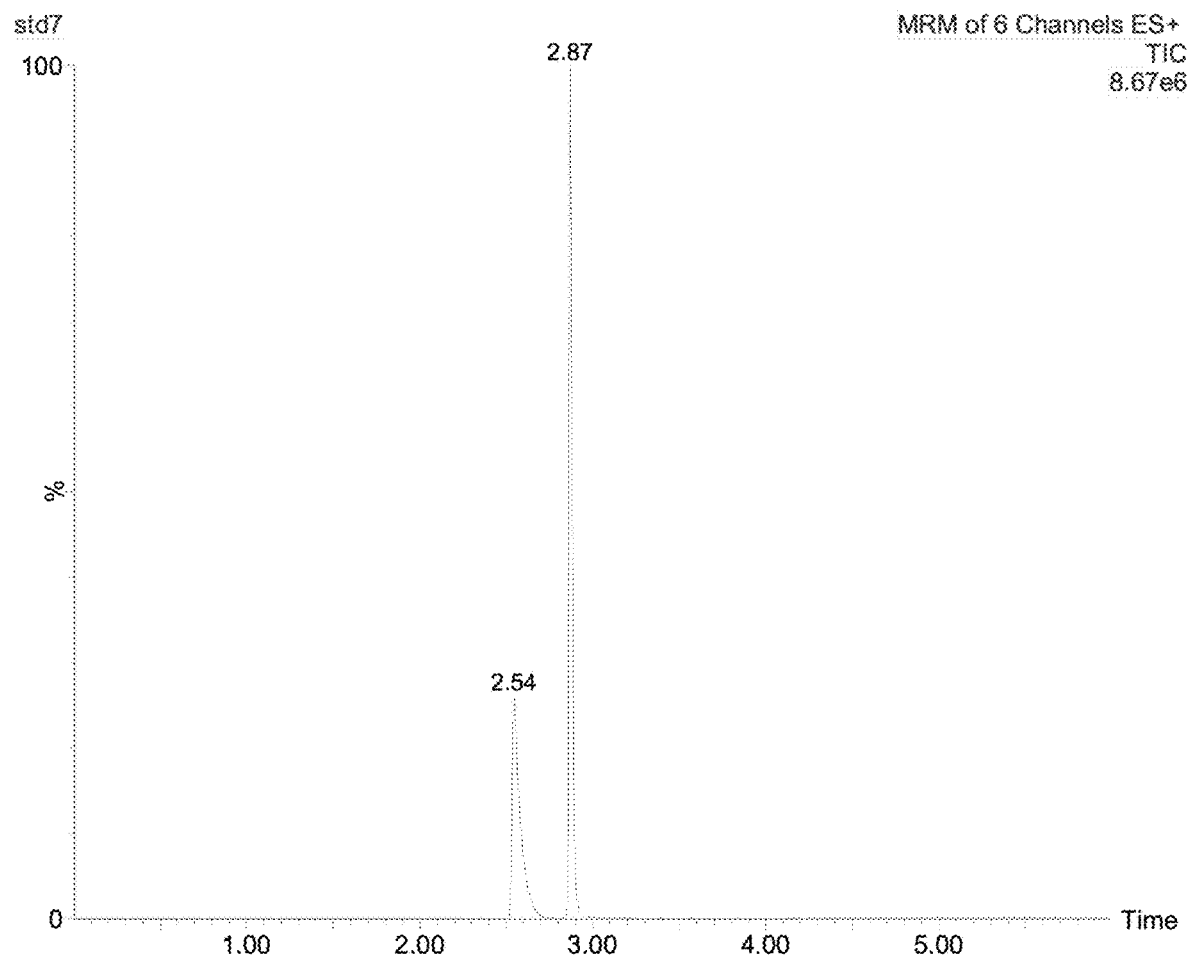
FIG. 22 shows the total ion flow of the standard.
Figure 23:
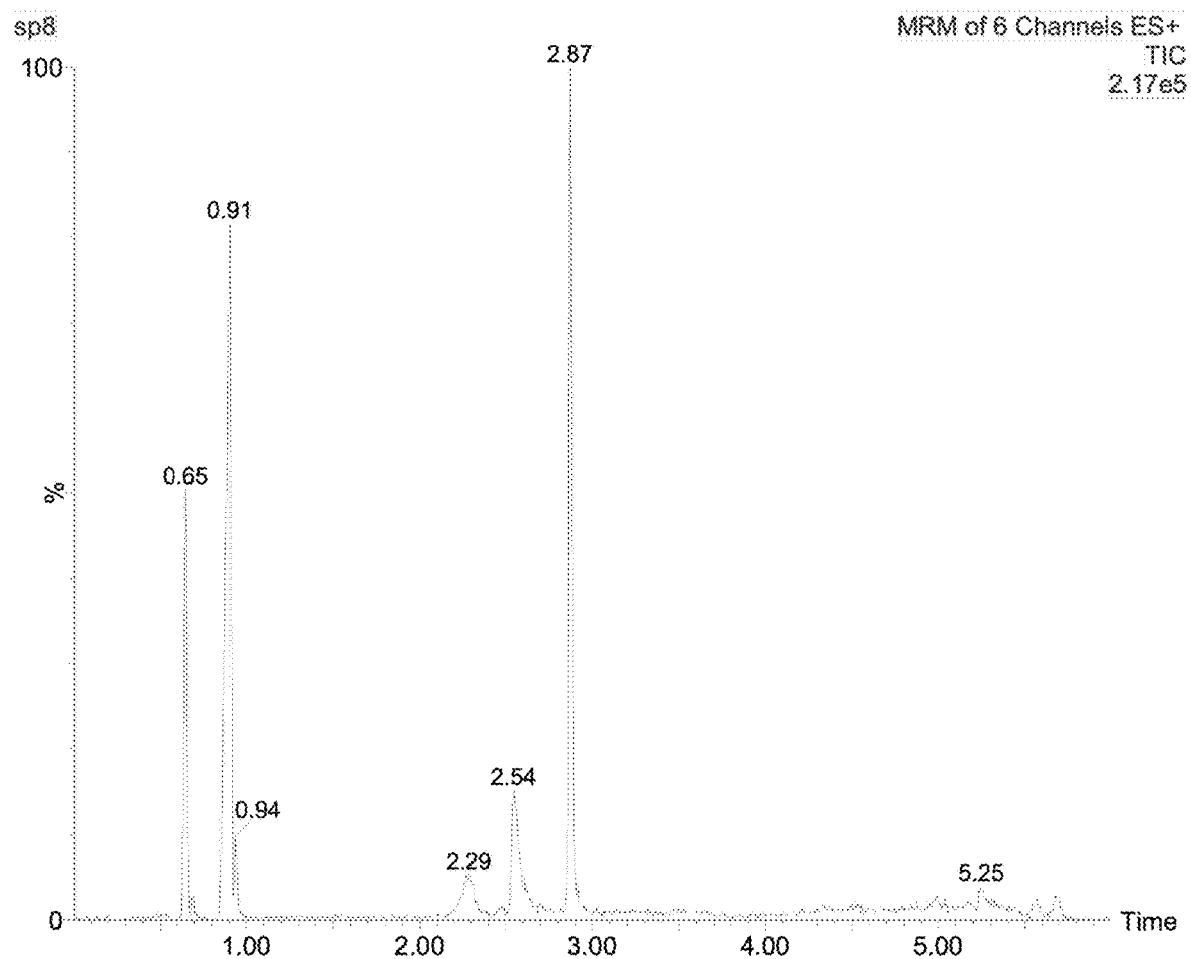
FIG. 23 shows the total ion flow of a sample.

4.4.2 Sturgeon Roe Tetrapeptide (NLPL SEQ ID NO: 9) Absorption Experiment in Rats 4.4.2.1 Polypeptide Standard and Sample Ion Flow Results are shown in FIGS. 21-23. Wherein the structure of the polypeptide standard is shown in FIG. 21, the total ion flow of the standard is shown in FIG. 22, and the total ion flow of the sample is shown in FIG. 23.

Figure 24:
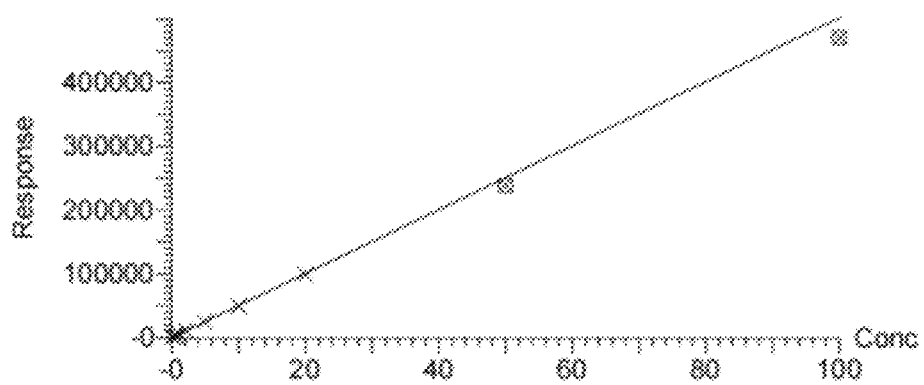
FIG. 24 shows a curve of a corresponding standard.

4.4.2.2 Polypeptide Standard Curves and Determination of Polypeptide Content in Blood Samples The corresponding standard curves are shown in FIG. 24.

It can be seen from FIG. 24 that the NLPL (SEQ ID NO: 9) shows good standard curve properties under this liquid chromatography-mass spectrometry combined method, and $R^2$ of 0.9996 indicates that the method has high accuracy in the determination of NLPL (SEQ ID NO: 9) content in samples.

Figure 25:
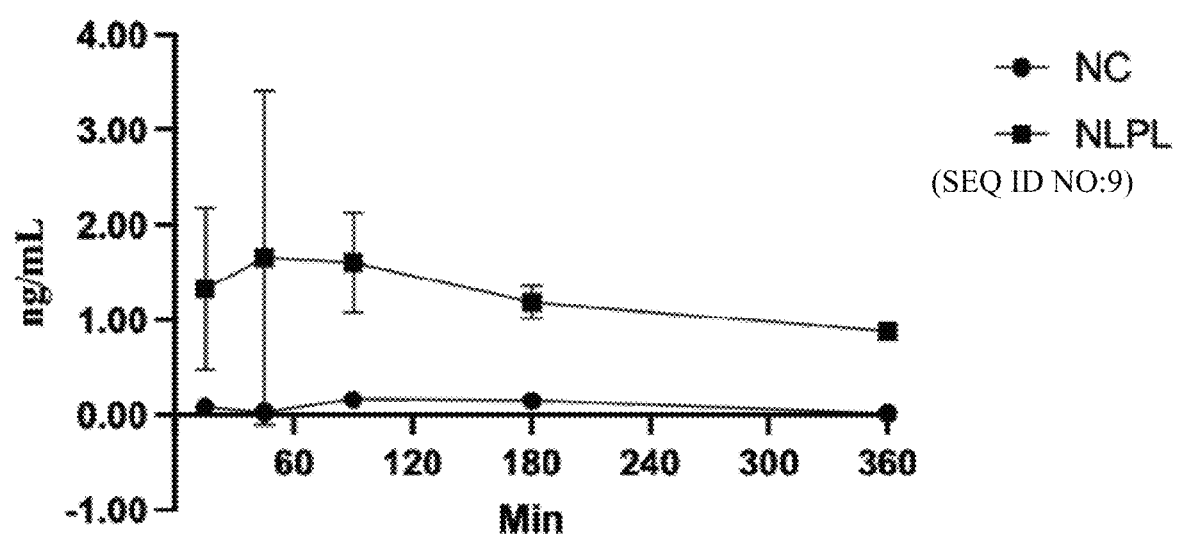
FIG. 25 shows the in vivo absorption condition of sturgeon roe tetrapeptide NLPL (SEQ ID NO: 9).

4.4.2.3 Detection of Sturgeon Roe Tetrapeptide Content in Rat Blood Samples at Different Time Points The absorption of the sturgeon roe tetrapeptide NLPL (SEQ ID NO: 9) in the body is shown in FIG. 25.

It can be seen from FIG. 25 that the NLPL (SEQ ID NO: 9) content in the blood of rats reaches a maximum within 45 min, which is 1.65±1.75 ng/mL. After 45 min, the NLPL (SEQ ID NO: 9) content shows a slow downward trend and is stabilized at about 0.88=0.00 ng/ml at 360 min. According to the AUC results, the AUC of the blank group is 34.39±0.00, while the AUC of the NLPL (SEQ ID NO: 9) group is 428.6±58.35 during the measurement time. Therefore, compared with the blank group, the NLPL (SEQ ID NO: 9) content in the blood is significantly increased. It can be known in combination with the animal experimental content that the NLPL (SEQ ID NO: 9) content plays an important role in oxidation resistance and improvement of skin aging in aging mice. From the structural information and the predicted results of enzyme digestion, the NLPL (SEQ ID NO: 9) may be cut into two dipeptides of NL and PL in the process of gastrointestinal digestion, resulting in lower NLPL (SEQ ID NO: 9) content than intragastric administration content. NL and PL show inhibitory activity against ACE and DPP-IV respectively.

The above description of the disclosed embodiments enables those skilled in the art to realize or use the present invention. Many modifications made to these embodiments will be apparent to those skilled in the art. General principles defined herein can be realized in other embodiments without departing from the spirit or scope of the present invention. Therefore, the present invention will not be limited to these embodiments shown herein, but will conform to the widest scope consistent with the principles and novel features disclosed herein.

SEQUENCE LISTING

```
Sequence total quantity: 14
SEQ ID NO: 1                  moltype = AA  length = 4
FEATURE                       Location/Qualifiers
source                        1..4
                              mol_type = protein
                              note = Peptide Fragments of Sturgeon
                              organism = synthetic construct
SEQUENCE: 1
LLLP                                                                           4

SEQ ID NO: 2                  moltype = AA  length = 4
FEATURE                       Location/Qualifiers
source                        1..4
                              mol_type = protein
                              note = Peptide Fragments of Sturgeon
                              organism = synthetic construct
SEQUENCE: 2
ALLP                                                                           4

SEQ ID NO: 3                  moltype = AA  length = 4
FEATURE                       Location/Qualifiers
source                        1..4
                              mol_type = protein
                              note = Peptide Fragments of Sturgeon
                              organism = synthetic construct
SEQUENCE: 3
LKFL                                                                           4

SEQ ID NO: 4                  moltype = AA  length = 4
FEATURE                       Location/Qualifiers
source                        1..4
                              mol_type = protein
                              note = Peptide Fragments of Sturgeon
                              organism = synthetic construct
SEQUENCE: 4
TGLW                                                                           4

SEQ ID NO: 5                  moltype = AA  length = 4
FEATURE                       Location/Qualifiers
source                        1..4
                              mol_type = protein
                              note = Peptide Fragments of Sturgeon
                              organism = synthetic construct
SEQUENCE: 5
LQPL                                                                           4

SEQ ID NO: 6                  moltype = AA  length = 4
FEATURE                       Location/Qualifiers
source                        1..4
                              mol_type = protein
                              note = Peptide Fragments of Sturgeon
                              organism = synthetic construct
SEQUENCE: 6
RLPF                                                                           4

SEQ ID NO: 7                  moltype = AA  length = 6
FEATURE                       Location/Qualifiers
source                        1..6
                              mol_type = protein
                              note = Peptide Fragments of Sturgeon
                              organism = synthetic construct
SEQUENCE: 7
AVLGPL                                                                         6

SEQ ID NO: 8                  moltype = AA  length = 4
FEATURE                       Location/Qualifiers
source                        1..4
                              mol_type = protein
                              note = Peptide Fragments of Sturgeon
                              organism = synthetic construct
SEQUENCE: 8
LGPL                                                                           4

SEQ ID NO: 9                  moltype = AA  length = 4
FEATURE                       Location/Qualifiers
source                        1..4
                              mol_type = protein
                              note = Peptide Fragments of Sturgeon
```

```
                        organism = synthetic construct
SEQUENCE: 9
NLPL                                                                    4

SEQ ID NO: 10           moltype = AA  length = 4
FEATURE                 Location/Qualifiers
source                  1..4
                        mol_type = protein
                        note = Peptide Fragments of Sturgeon
                        organism = synthetic construct
SEQUENCE: 10
GLPL                                                                    4

SEQ ID NO: 11           moltype = AA  length = 4
FEATURE                 Location/Qualifiers
source                  1..4
                        mol_type = protein
                        note = Peptide Fragments of Sturgeon
                        organism = synthetic construct
SEQUENCE: 11
WSLL                                                                    4

SEQ ID NO: 12           moltype = AA  length = 7
FEATURE                 Location/Qualifiers
source                  1..7
                        mol_type = protein
                        note = Peptide Fragments of Sturgeon
                        organism = synthetic construct
SEQUENCE: 12
ALPLDPK                                                                 7

SEQ ID NO: 13           moltype = AA  length = 4
FEATURE                 Location/Qualifiers
source                  1..4
                        mol_type = protein
                        note = Peptide Fragments of Sturgeon
                        organism = synthetic construct
SEQUENCE: 13
KYPL                                                                    4

SEQ ID NO: 14           moltype = AA  length = 9
FEATURE                 Location/Qualifiers
source                  1..9
                        mol_type = protein
                        note = Peptide Fragments of Sturgeon
                        organism = synthetic construct
SEQUENCE: 14
VDNHVPLRL                                                               9
```

What is claimed is:

1. A method of preparing an anti-aging sturgeon roe tetrapeptide consisting of the amino acid sequence of NLPL (SEQ ID NO: 9), wherein the method comprises:
    (1) adding deionized water to sturgeon roes and homogenizing to obtain a sturgeon roe homogenate;
    (2) adjusting pH value of the sturgeon roe homogenate, adding alkaline protease, performing enzymolysis, inactivating the alkaline protease, and cooling to obtain sturgeon roe enzymatic hydrolysate; and
    (3) centrifuging the sturgeon roe enzymatic hydrolysate, taking a supernatant to obtain the anti-aging sturgeon roe tetrapeptide, and storing the anti-aging sturgeon roe tetrapeptide for later use.

2. The method according to claim 1, wherein in step (1), mass ratio of the sturgeon roes to the deionized water is 1:6.

3. The method according to claim 1, wherein in step (1), the homogenizing is performed at rotational speed of 8000 rpm for 1 minute.

4. The method according to claim 1, wherein in step (2), the alkaline protease is at a concentration of 1% (W/W).

5. The method according to claim 1, wherein in step (2), the enzymolysis is performed at a temperature of 55° C. for 8 hours.

6. The method according to claim 1, wherein in step (2), the inactivating the alkaline protease is performed at a temperature of 90-100° C. for 10-15 minutes; and the cooling is performed until the sturgeon roe enzymatic hydrolysate is at room temperature.

7. The method according to claim 1, wherein in step (3), the centrifugation is performed at a temperature of 4° C. and a rotational speed of 8000 rpm for 15 minutes.

8. The method according to claim 1, wherein in step (3), the antiaging sturgeon roe tetrapeptide is stored at a temperature of −80° C.

* * * * *